Figure 1:
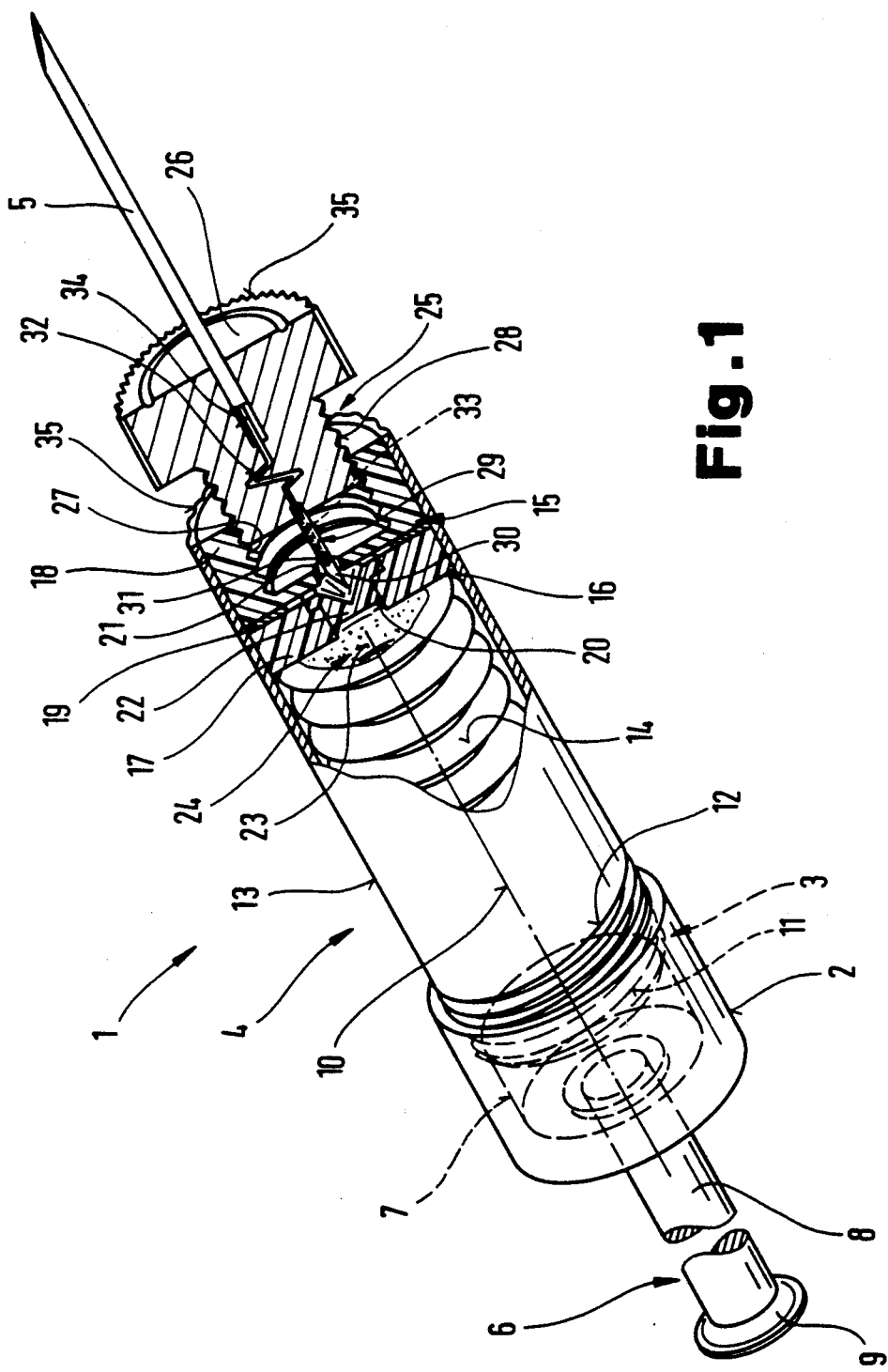

United States Patent [19]

Pickhard

[11] Patent Number: 5,147,311
[45] Date of Patent: Sep. 15, 1992

[54] INJECTION DEVICE FOR USE WITH A DEFORMABLE AMPOULE

[76] Inventor: Ewald Pickhard, Redtenbachergasse 15, A-1160 Vienna, Austria

[21] Appl. No.: 477,831
[22] PCT Filed: Aug. 29, 1988
[86] PCT No.: PCT/AT88/00068
   § 371 Date: May 3, 1980
   § 102(e) Date: May 3, 1980
[87] PCT Pub. No.: WO89/02286
   PCT Pub. Date: Mar. 23, 1989

[30] Foreign Application Priority Data
   Sep. 9, 1987 [AT] Austria ............................... 2289/87

[51] Int. Cl.⁵ ..................... A61M 5/24; A61M 5/315
[52] U.S. Cl. .................... 604/153; 604/131; 604/135; 604/148
[58] Field of Search ............ 604/155, 151, 131, 143, 604/133, 135, 134, 153, 148; 128/DIG. 12

[56] References Cited

U.S. PATENT DOCUMENTS

| | | | |
|---|---|---|---|
| 1,541,615 | 6/1925 | Bessesen | 604/143 |
| 3,372,697 | 3/1963 | Kellun | 604/241 |
| 3,605,744 | 9/1971 | Dwyer | 604/157 |
| 3,631,847 | 1/1972 | Hobbs, II | 604/155 |
| 3,701,345 | 10/1972 | Heilman et al. | 604/155 |
| 3,858,581 | 1/1975 | Kamen | 604/155 |
| 3,884,229 | 5/1975 | Raines et al. | 604/232 |
| 4,132,231 | 1/1979 | Puccio | 604/131 |
| 4,150,672 | 4/1929 | Whitney et al. | 604/155 |
| 4,437,859 | 3/1984 | Whitehouse et al. | 604/131 |
| 4,626,244 | 12/1986 | Reinickee | 604/141 |
| 4,681,566 | 7/1937 | Fenton, Jr. et al. | 128/DIG. 12 |
| 4,734,092 | 3/1988 | Mallerd | 128/DIG. 12 |
| 4,758,226 | 7/1988 | Carre | 604/141 |
| 4,781,683 | 11/1988 | Thoma et al. | 604/134 |
| 4,871,351 | 10/1989 | Feingold | 128/DIG. 12 |

FOREIGN PATENT DOCUMENTS

| | | |
|---|---|---|
| 162791 | 11/1985 | European Pat. Off. . |
| 170784 | 2/1986 | European Pat. Off. . |
| 2112654 | 10/1972 | Fed. Rep. of Germany . |
| 468196 | 3/1969 | Switzerland . |
| 2072017 | 9/1981 | United Kingdom . |

*Primary Examiner*—Paul J. Hirsch
*Attorney, Agent, or Firm*—Collard & Roe

[57] ABSTRACT

An injection device (1) has a housing (2) in which is arranged a holder for a deformable, medicament-containing ampoule (4). To a frontal end region is linked an injection needle (5) which communicates with the interior of the ampoule and with a driving device linked to the other frontal end region of the ampoule, opposite the frontal end region facing the injection needle. The ampoule (4) is arranged and held within a support device (13) that extends between both frontal end regions.

29 Claims, 11 Drawing Sheets

INJECTION DEVICE FOR USE WITH A DEFORMABLE AMPOULE

The invention concerns an injection device with a housing that accommodates a holder for a deformable ampoule that contains a medicament, with a hypodermic needle inserted in one end of the housing and communicating with the inside of the ampoule and with an activating mechanism at the end of the housing remote from the needle.

Various injection devices are known that a deformable ampoule can be employed in. One injection device of this type is known from European A1 0 170 784. It features a fold-up housing with accommodation for an ampoule in the form of a bellows. One end of the bellows is positioned directly in the housing and an activating mechanism is associated with the activating mechanism at the other end of the ampoule. The activating mechanism consists of a plunger that can be displaced toward the outlet by means of a spindle-and-traveling-nut device. The threaded spindle is rotated by an electric motor. A hypodermic needle can be inserted into the end of the ampoule that projects out of the housing. The medicament inside the ampoule can be forced out through the needle in a length of time that varies with how fast the piston travels. The bellows-type ampoule is difficult to handle when it is inserted in the housing. It is also impossible to control the dose of medicament.

Another type of injection device that employs a deformable ampoule is known from U.S. Pat. No. 4,525,164. This ampoule is in the form of a flexible tube arrayed in a semicircle and has a hypodermic needle at each end. A squeezing roller is positioned at the other end of the ampoule as the medicament inside it begins to be released. The medicament is released from the ampoule by rolling the roller toward the ampoule's needle end. The ampoule is accordingly squeezed between the roller and the opposite wall of the housing that accommodates the ampoule. As the roller advances toward the hypodermic needle, the medicament inside the ampoule is forced out through the needle. More or less medicament is injected through the needle depending on how rapidly the roller is advanced. The squeezing roller in this embodiment of the device is secured to a revolving ring that has teeth along one edge and engages a pinion driven by an electric motor. This deformable ampoule is also difficult to handle when inserted into the housing, and the dose of medicament injected through the needle is difficult to monitor.

Another injection device, known from European A2 0 178 371, also employs a bellows-type ampoule accommodated in a cylindrical housing, whereby one outside diameter and one length of the ampoule essentially equals one inside diameter and one inside length of a tubular housing. One end of the tubular housing is sealed to a base plate. A cap can be screwed into the tubular housing from the other end. Between the base plate and the cap is a resiliently deformable ampoule. Screwing the cap into the tubular housing forces the medicament out of the ampoule and into the needle. Inserting the deformable ampoule into this embodiment of an injection device also demands very careful handling, and the dosage precision is inadequate in many situations. The object of the present invention is to provide an injection device that will facilitate handle deformable ampoules when they are employed with it and that will itself also be easy to use.

This object is attained in accordance with the invention in that the ampoule is positioned and secured in a support that extends from one end of the housing to the other.

The major advantage of this approach is that the support makes it possible to employ plastic ampoules that are just as easy to handle as glass ampoules. Furthermore, it is easier to control the flow of the medicament in the ampoule in that the ampoule is secured in the support while it is being deformed to force out the medicament, and the support can be designed to secure it in that way. Another and surprising advantage of this approach is that the ampoules do not have to have pistons inside them that have to be sealed off. The component that deforms the ampoule can also be accommodated in the support, keeping the cost of the housing of an injection device that employs this type of deformable ampoule very low.

The main section of the ampoule in one embodiment of the invention is shaped like a sack, is in particular made of plastic, and is connected to a combination seal and holder as its open end. The medicament inside the ampoule is accordingly always forced toward the combination seal and holder, toward the open end of the ampoule, that is. This system prevents the medicament from leaking out of the ampoule where the ampoule is engaged by the activating mechanism.

It is on the other hand also possible for the main section to be a plastic bellows that is connected to a combination seal and holder at least one of its two ends. An ampoule in the form of a bellows will eject the medicament more uniformly and will not become jammed between the activating mechanism and the support.

It is also an advantage for the combination seal and holder to be in one piece with the ampoule.

It is, however, also possible for the combination seal and holder to be made of a stable main plastic section and in particular to be welded to the ampoule. This arrangement will prevent stress on the main section of the ampoule from the forces the secure the ampoule in the holder, especially when the hypodermic needle is being inserted and when the medicament is being injected. These supporting forces will on the other hand be accommodated by the stabile main plastic section.

The combination seal and holder on the ampoule in another variation of this embodiment is secured stationary in and in particular welded or cemented into the support. This characteristic ensures adequate backing for the support along the direction the medicament is injected in and simplifies the design of both the injection device and its housing as well as the process of inserting the ampoule. It is, however, also possible for the combination seal and holder to be in two parts with a barrier, a diaphragm for example, between them. The combination seal and holder can accordingly also act as a safety seal and make it possible to do without a separate safety seal.

The combination seal and holder in another version of this embodiment has an attachment for a needle holder. This makes it possible to attach the hypodermic needle to the ampoule only just before injecting the medicament.

It is, however, also of advantage for the attachment to consist of one half that comprises a bore with an inside thread in the combination seal and holder and of another half that comprises an outside thread on the needle holder and to extend preferably parallel to the longitudinal axis of the ampoule or the outlet therefrom. This system ensures that the needle holder will be reliably secured and that the seal between the ampoule and the hypodermic needle will be tight.

In another variation of this embodiment a perforator can be accommodated in the needle holder and or in the combination seal and holder and or in a spacer that extends between them, and the position of the perforator can be varied relative to the barrier. This system ensures that the medicament in the ampoule will be safe until ready for use.

It is, however, also of advantage for the needle carrier and/or the combination seal and holder and/or the spacer to have a constricting channel that connects the inside of the ampoule with the hypodermic needle. This system ensures that only a definite and prescribed volume of medicament can be forced out of the ampoule per unit of time no matter what the pressure inside the main section of the ampoule is. The approach prevents incorrect dosage, and the dose can be simply adjusted by varying the constricting channel to the amount of medicament needed in each particular case.

It is, however, also possible for the support to be tubular and especially to have a round cross-section. When, accordingly, the bellows-type ampoule has a round cross-section, it can slide back and forth without much friction and ampoules that have tubular supports can also be employed instead of glass ampoules with a round cross-section.

It is also of advantage for the ampoule to be tubular, especially with a round cross-section. This makes it possible to position the deformable ampoule all the way around and accordingly reliably prevent undesirable deformations that might cause the ampoule to become jammed in the support.

The outside diameter of the ampoule in another version of this embodiment essentially equals the inside diameter of the support or of an enveloping circle tangent to the inner surface thereof. This characteristic makes it possible to use ampoules with a thinner-walled main section because the ampoule will be reliably prevented from yielding radially by the support.

The support in another version of this embodiment has a track that essentially parallels the longitudinal axis of the ampoule. This approach simplifies positioning both the support and the activating mechanism that compresses the ampoule.

It is in the embodiment possible for the track to extend from the end of the ampoule that is farthest from the combination seal and holder to the transition between the ampoule and the combination seal and holder. This approach makes it possible to position the activating mechanism, a piston that compresses the ampoule for example, precisely in relation to the ampoule over the whole stroke traveled by the activating mechanism in compressing the ampoule.

It is, however, also of advantage for the track to consist of two slots, preferably in the vicinity of the points of intersection of a diametrical with mutually facing areas of the walls of the support. This allows the ampoule to be compressed along a straight beam that extends beyond the support and can be positioned or subjected to tension or compression on each side of the support.

It is also possible for the perforator for the needle carrier to more or less parallel the hypodermic needle. In this design the barrier in the ampoule is broken through when the needle is inserted.

It is also possible for the perforator for the needle carrier to be more or less perpendicular to the hypodermic needle and parallel to the longitudinal axis of the ampoule. This arrangement makes it possible to exploit the motion that occurs in inserting the needle to break through the barrier and also allows the needle to extend radially, which saves space in particular in injection devices that are secured to the human body for a long period of time.

This is especially applicable when the hypodermic needle is perpendicular to the longitudinal axis of the ampoule.

The support for the ampoule can be accommodated in a holder in the housing, and a piston that slides back and forth along the support or ampoule can be associated with the inside of the support and forced by the activating mechanism toward the combination seal and holder. The support can accordingly be exploited not only to position and support the outer surface of the deformable ampoule but also to align the piston that deforms the ampoule. The system also prevents damage to the ampoule while it is being deformed.

It is also of advantage for the piston to have tracking components that engage the track in the support. This approach prevents radial forces from acting on the ampoule.

The support and/or the needle holder can rest against a backing, especially the housing, in the injection device and the stroke traveled by the piston in the activating mechanism can be at least as long as the track. The piston in the activating mechanism can accordingly not impede insertion of the activating mechanism or ampoule in the housing.

The activating mechanism can comprise an activator, a spring for example, on each side of the support. This system deforms the ampoule at the center.

A mechanism, a strap for example, can be employed to arrest the motion of the activating mechanism and to fix the piston in a limiting position that is remote from the support. This system facilitates inserting the ampoule or support, especially when the activator is a spring.

It is also of advantage for the housing of the injection device to be in two parts with an opening for the hypodermic needle in the base plate. The ampoule can then be inserted into the housing from above and correctly positioned, after which the housing can be closed.

One end of the ampoule can have a recess that extends away from the needle holder and along the ampoule as far as the perforator projects into the ampoule minus the distance of the ampoule when the bellows is compressed. The recess allows the depth of penetration of the perforator to be varied to ensure access on the part of the medicament into the channel that extends out into the hypodermic needle without the part of the inside of the ampoule that cannot be completely emptied having to be too large.

It is also practical for the piston in the activating mechanism to have an opening that accommodates the continuation of the ampoule. This system always prevents the perforator from damaging the side of the ampoule facing the piston.

The perforator can be a pusher that travels back and forth perpendicular to the barrier and is fastend to the needle holder and/or the combination seal and holder and/or a spacer by way of a security mechanism. This system provides twice as much security against reuse of the injection device.

The activating mechanism can be a threaded-spindle drive mechanism, especially one that parallels the longitudinal axis of the ampoule, and the piston can be coupled to it with traveling nuts.

The activating mechanism can be a fluid-charged piston-and-cylinder mechanism. This approach ensures as tight and continuous a force on the ampoule as possible.

The injection device can also have a pressure resevior and/or a compressor and/or a vacuum pump associated with the activating mechanism. The pressure exerted by the fluid can accordingly be exploited in a simple way to control the amount of medicament injected.

Controls can be associated with the ampoule and connected to the activating mechanism and/or to limit switches associated with the ampoule and/or to an adder and/or to a lamp and optionally to a flowmeter. This system makes it possible to monitor the action of the activating mechanism and the amount of medicament injected and make any malfunctions immediately apparent visually or aurally. The operator of the injection device can also accordingly be informed in a simple way that a new ampoule must be inserted to reliably prevent medical drawbacks for the patient.

Sensors accommodated in the housing and or in a strip associated with it can be associated with the controls and can measure such data as the patient's pulse, blood pressure, temperature, etc. The dosage of medicament from the ampoule can accordingly be matched to the needs of the patent.

It is also practical for a motion detector to be associated with the housing and connected to the controls, which include a stage that varies the amount of medicament supplied to the hypodermic needle in accordance with motion. The dosage of medicament can accordingly be matched to the patient's activity so that more or less can be administered when he begins to move.

The needle holder and/or the spacer can consist of two parts, preferably separated along a plane perpendicular to the longitudinal axis, and the constricting channel can be a depression in one part, with the open side of the depression being covered up by the other part. This makes it possible in a simple way to make very thin channels with bends.

Another version of this embodiment features a microfilter between the perforator and the hypodermic needle, and the side of the microfilter that faces the hypodermic needle can preferably cover up the constricting channel. This is a simple way of preventing very fine particles from entering the hypodermic needle and hence the patient's body. The design can be additionally exploited by sealing off the constricting channel with the microfilter.

The constricting channel in one of the parts can consist of several annular-channel sections concentric with the longitudinal axis of the ampoule and differing in diameter, each extending at an angle of 270° for example and communicating alternately and radially. This design simplifies the manufacture of the constricting channel, and a relatively long channel can be accommodated in a relatively small area.

The constricting channel in one of the parts can be a helical channel concentric with the longitudinal axis of the ampoule. This eliminates sharp angles in the constricting channel.

The microfilter can consist of a securing ring and a tensioning gasket with a membrane secured between them, whereby the inside diameter of an annular flange on the securing ring equals the outside diameter of the tensioning gasket. This embodiment features few parts.

It is also of advantage for the mutually facing inner and outer circumferential surfaces of the tensioning gasket and the securing ring to fit together tight. Securing the filter membrane to the tensioning gasket will accordingly also secure it to the securing ring.

It is also of advantage for the ampoule to be a glass ampoule with a Luer cone and a sealing ring between one edge of the Luer cone and a mounting structure, whereby the sealing ring is a rubber component with a mounting pin that extends into an outlet from the Luer cone and into a mounting opening of the mounting structure for the needle holder. The microfilter can accordingly be tightly and reliably secured in the injection outlet.

Other advantageous embodiments of the invention are recited in the subsidiary claims.

Figure 3:
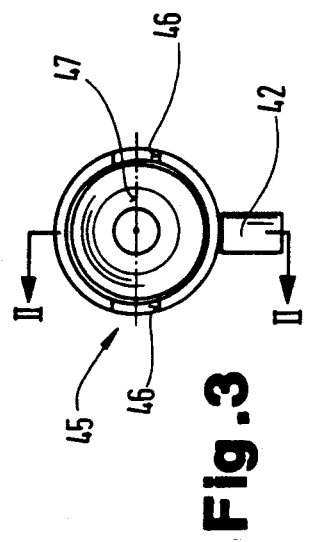
Figure 2:
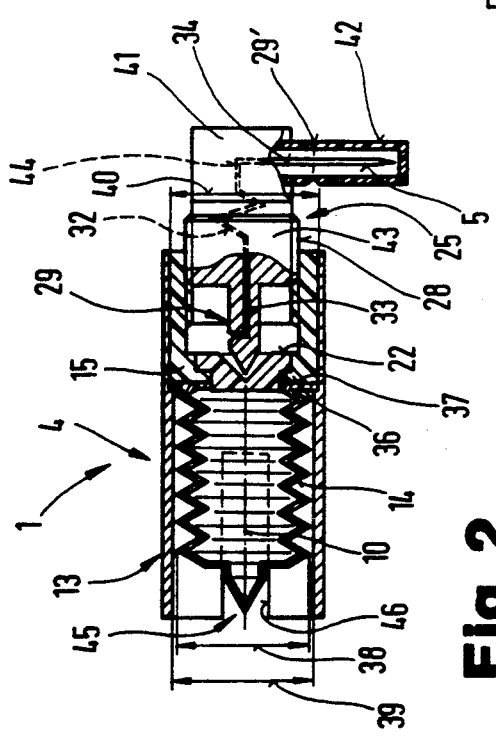
Figure 4:
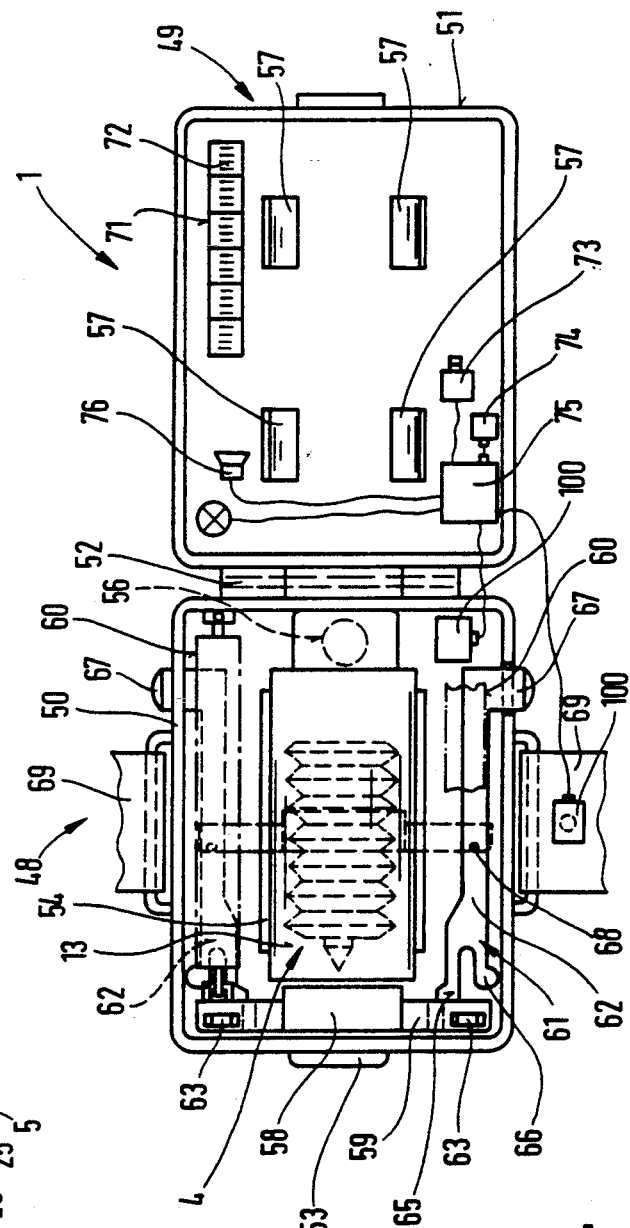
Figure 5:
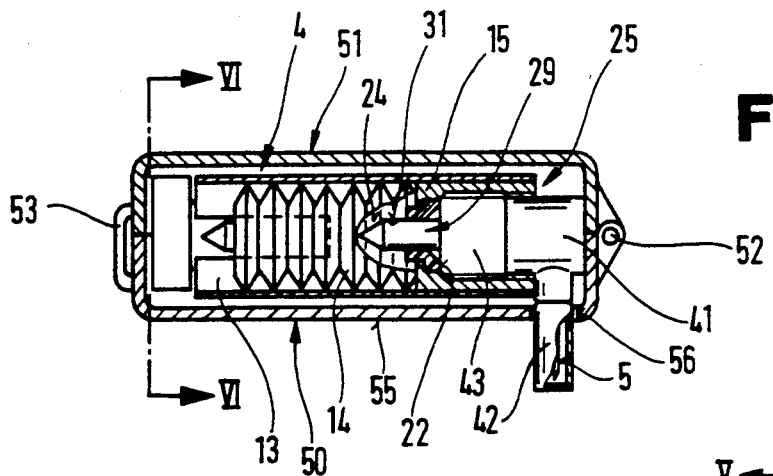
Figure 6:
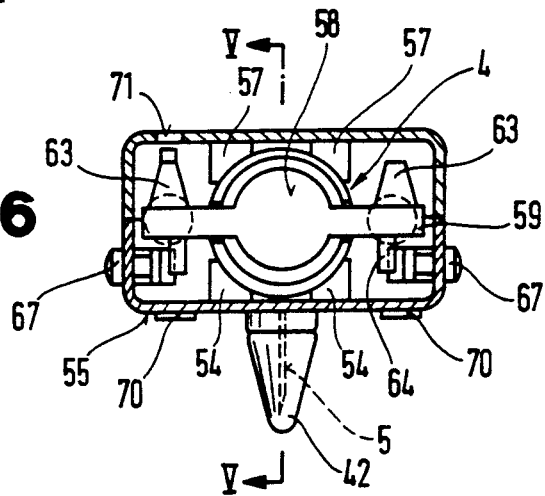
Figure 7:
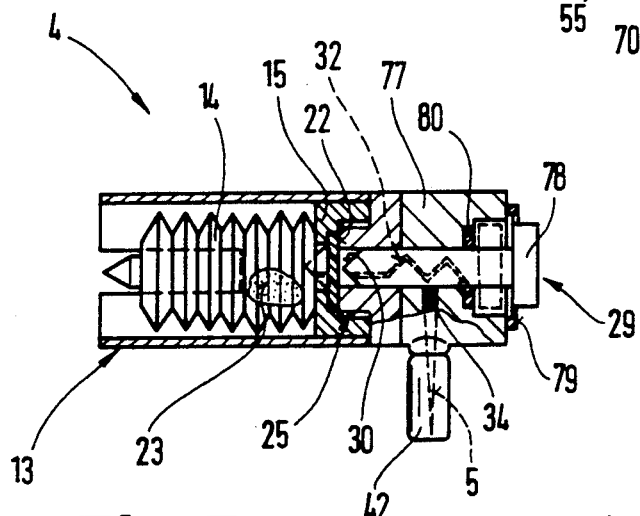
Figure 8:
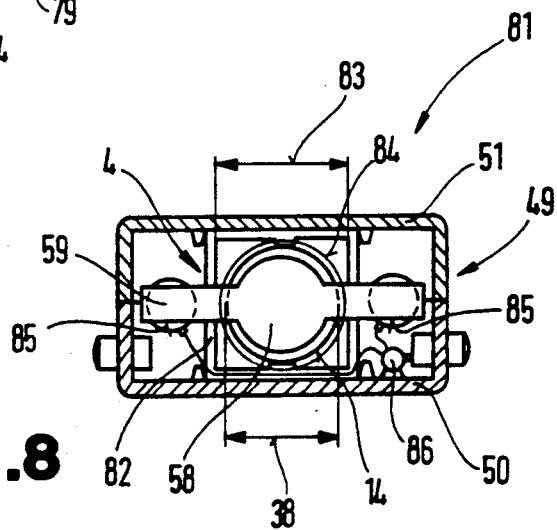
Figure 9:
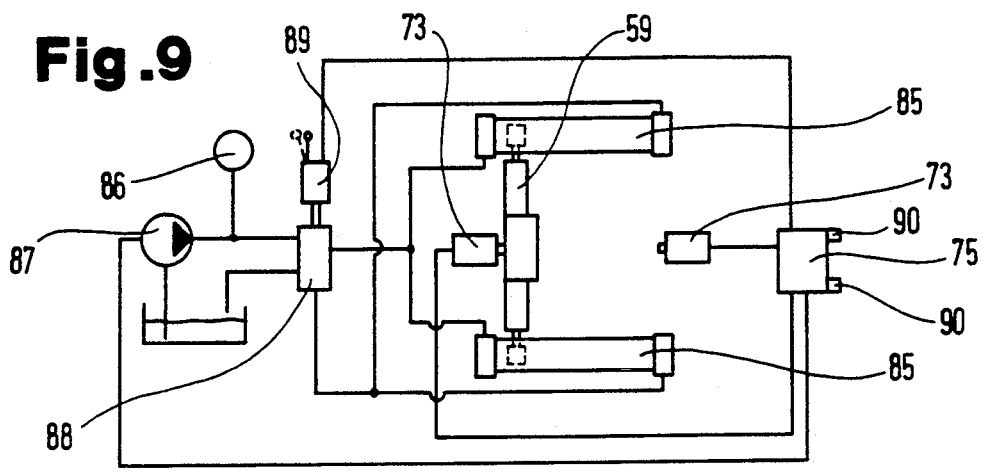
Figure 10:
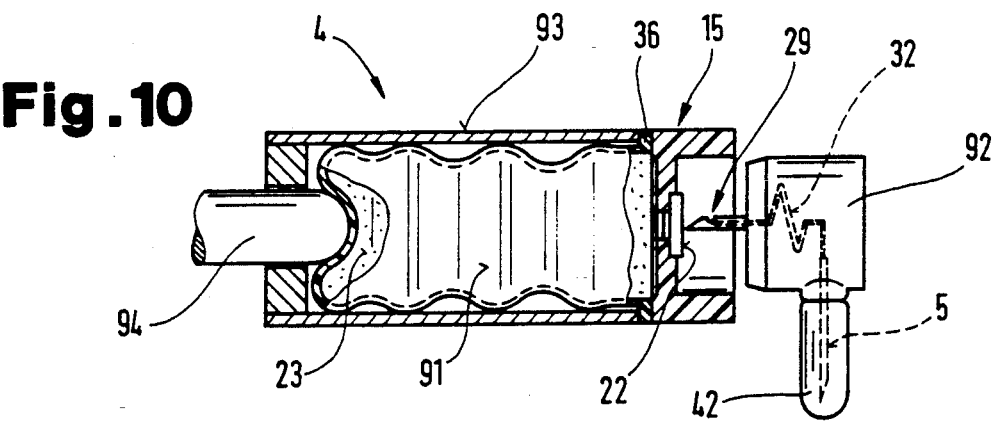
Figure 11:
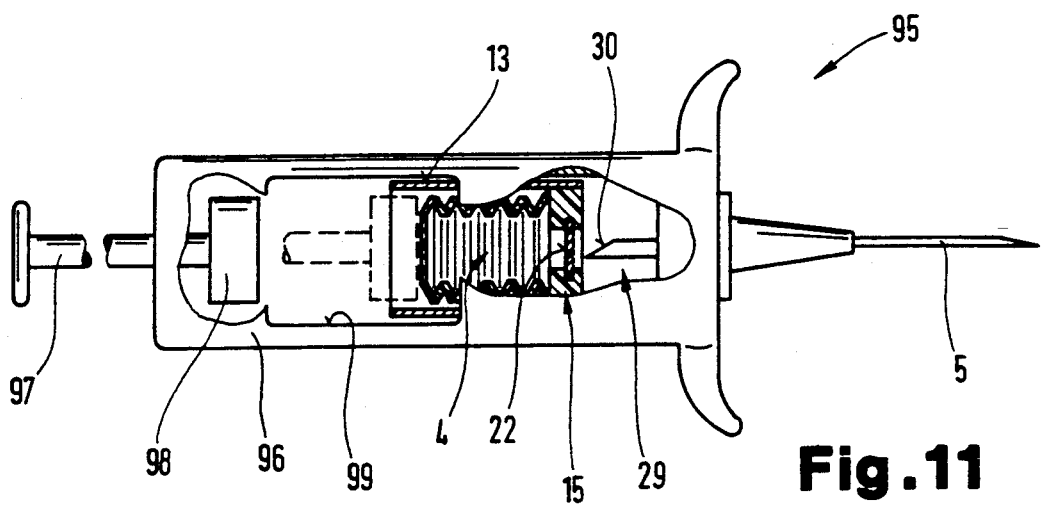
Figure 12:
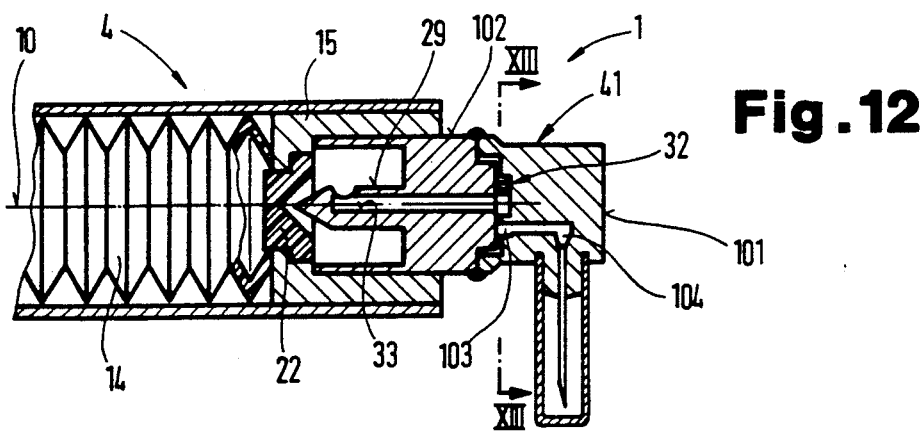
Figure 14:
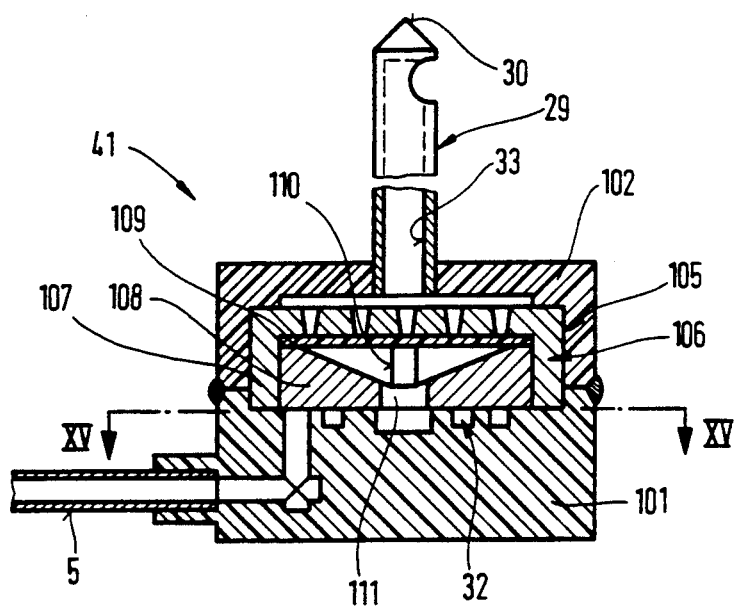
Figure 13:
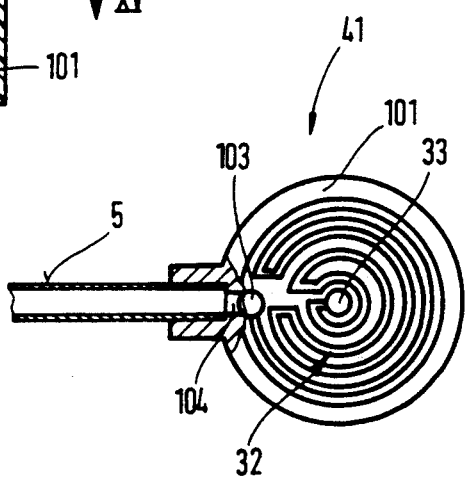
Figure 15:
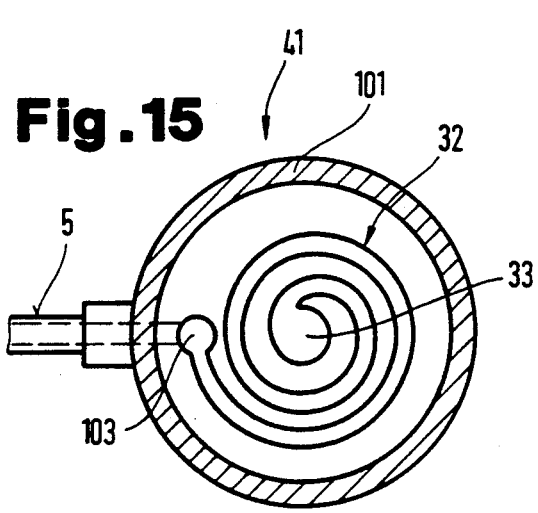
Figure 16:
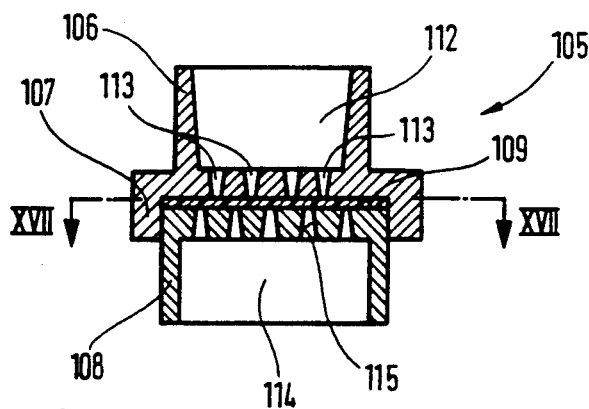
Figure 17:
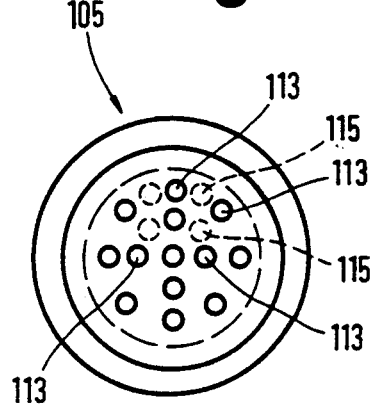
Figure 18:
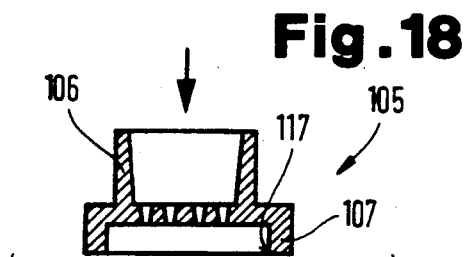
Figure 19:
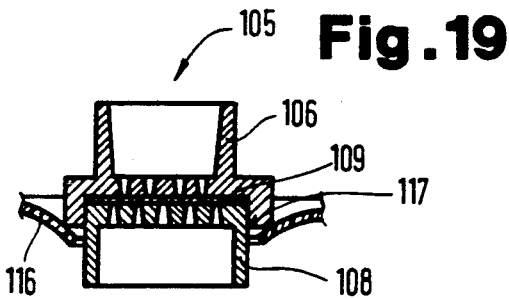
Figure 20:
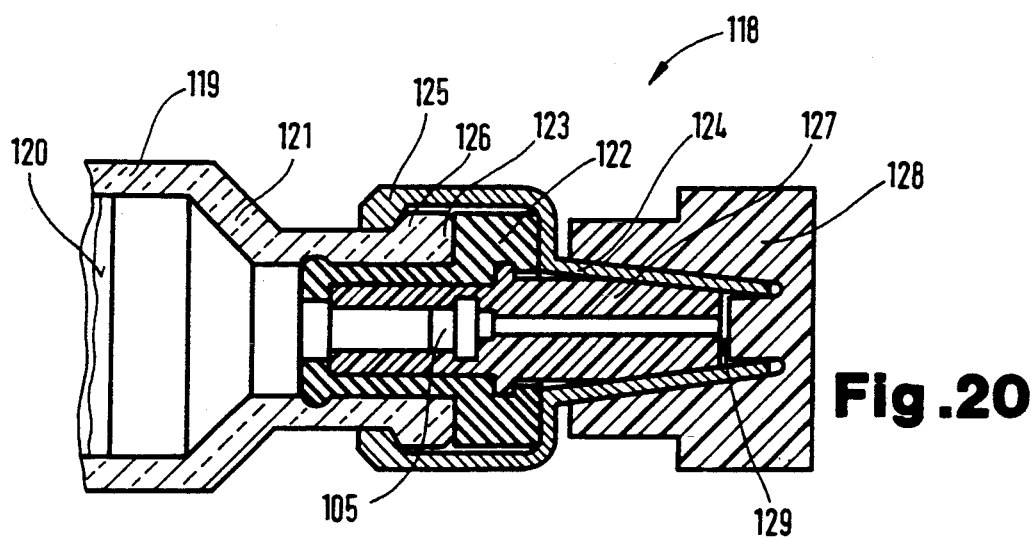
Figure 21:
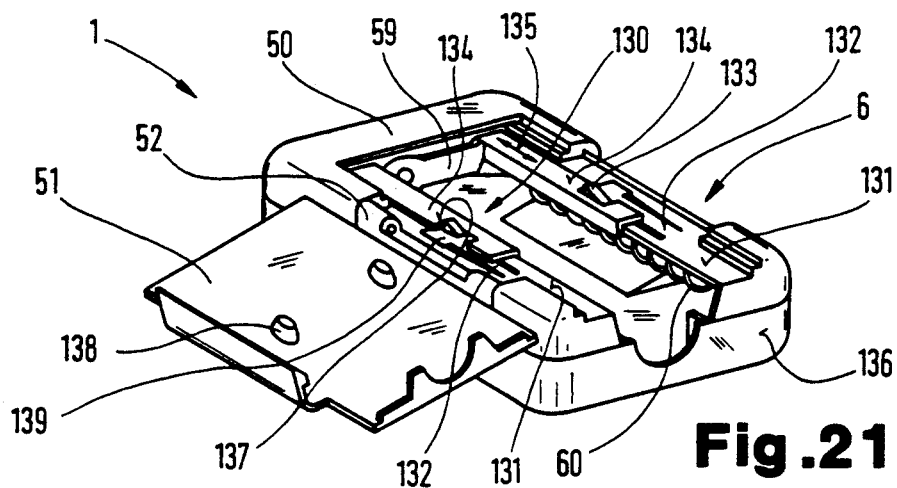
Figure 22:
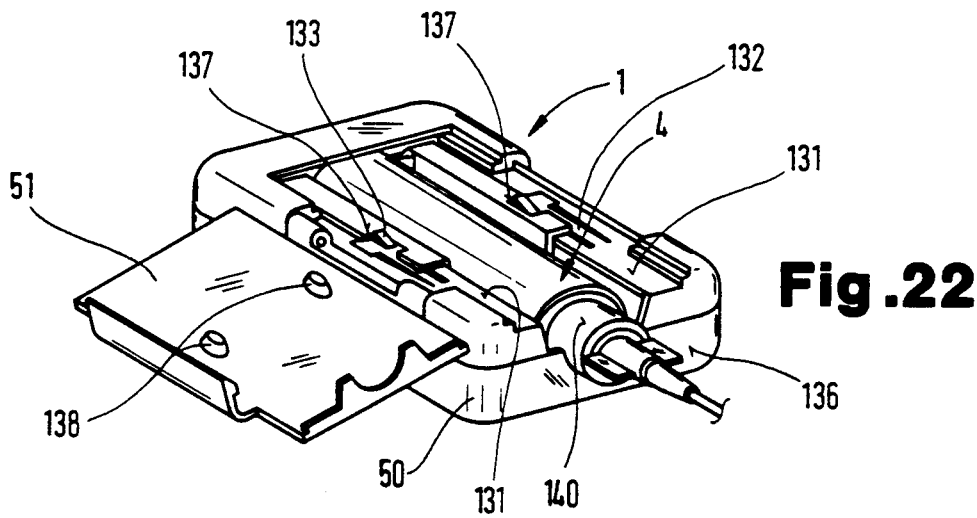
Figure 23:
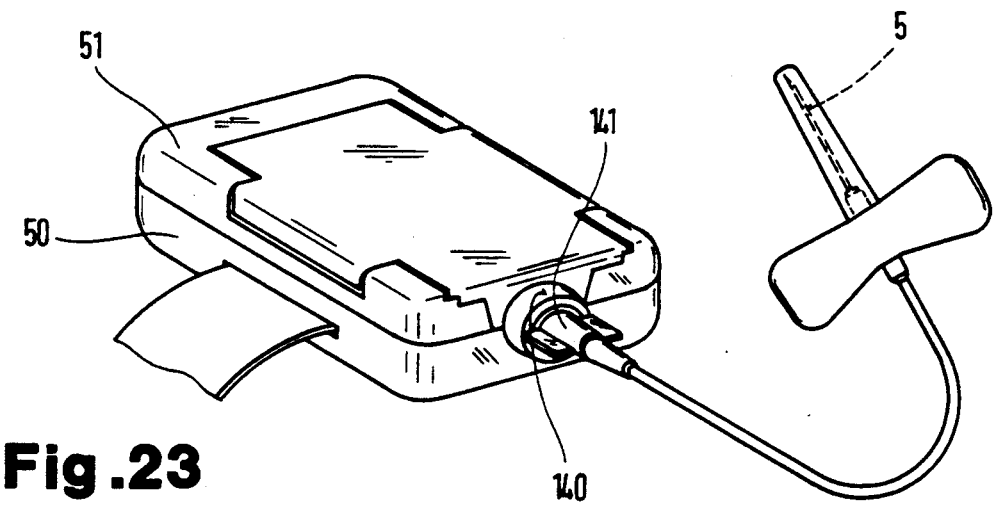
Figure 24:
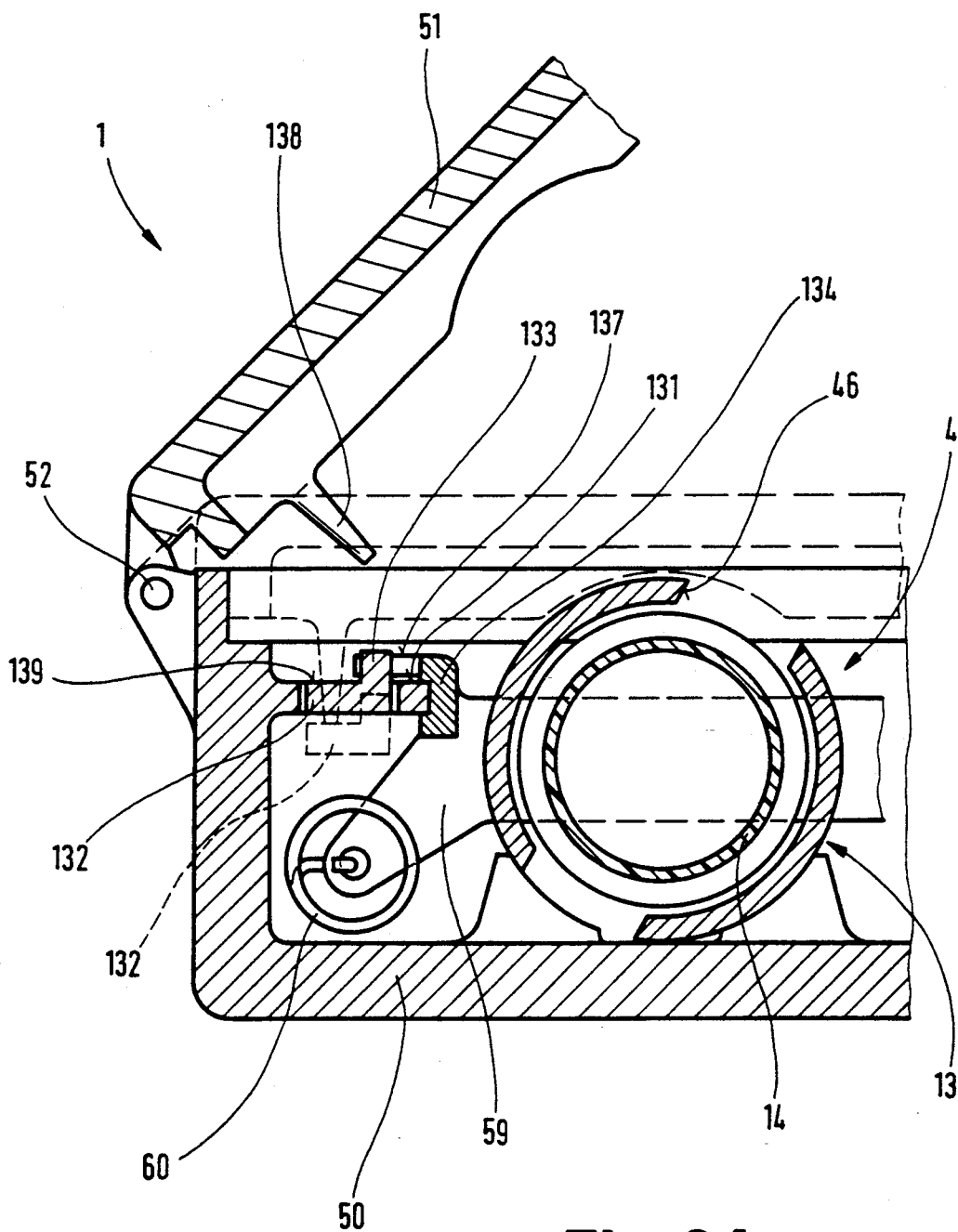
Figure 25:
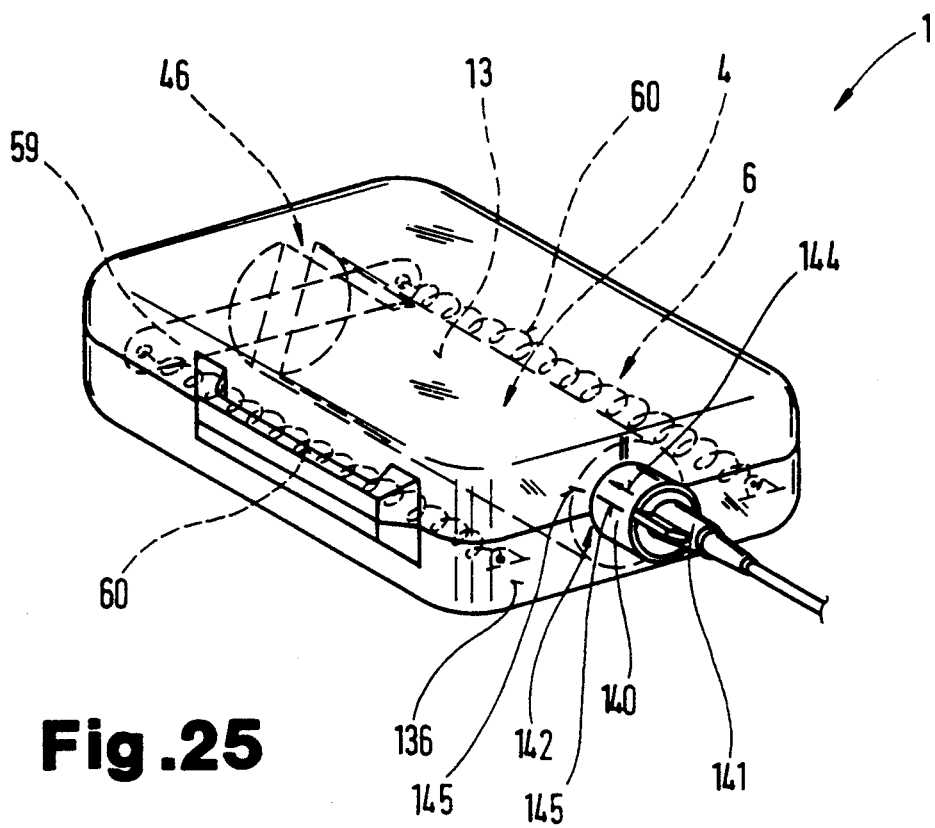
Figure 26:
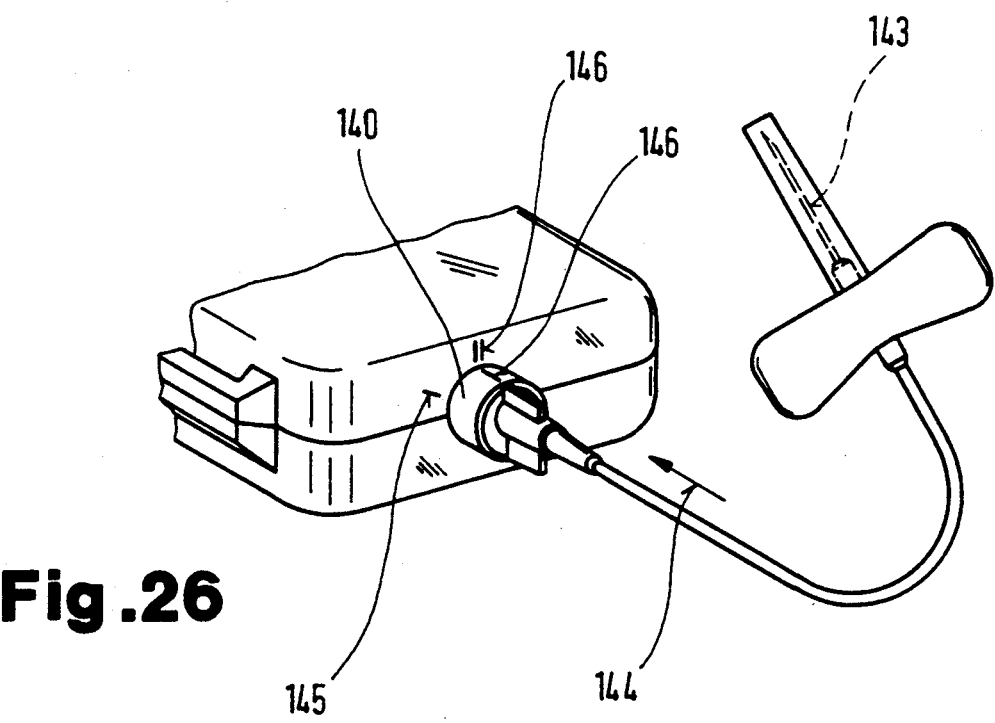
Figure 27:
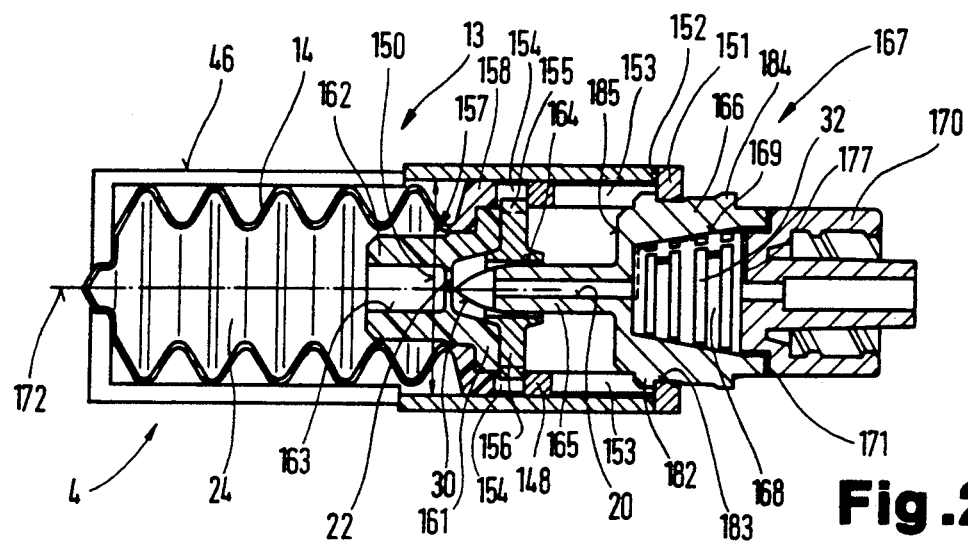
Figure 28:
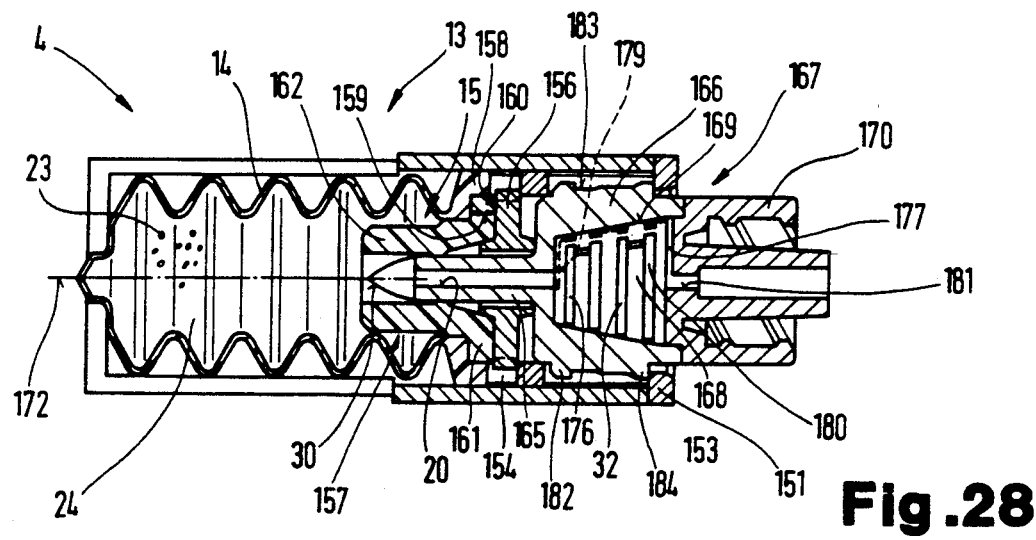
Figure 29:
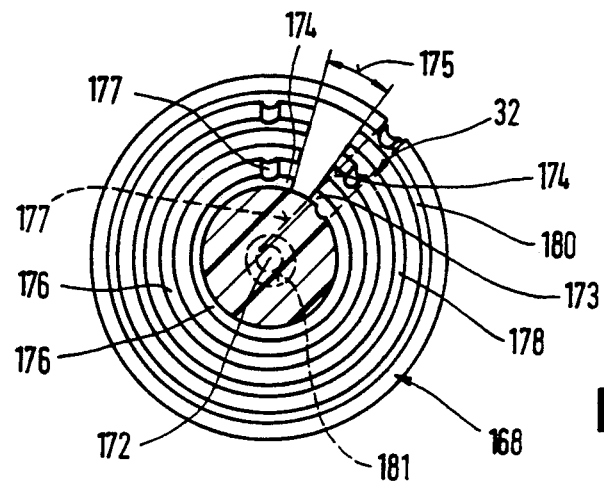
Figure 31:
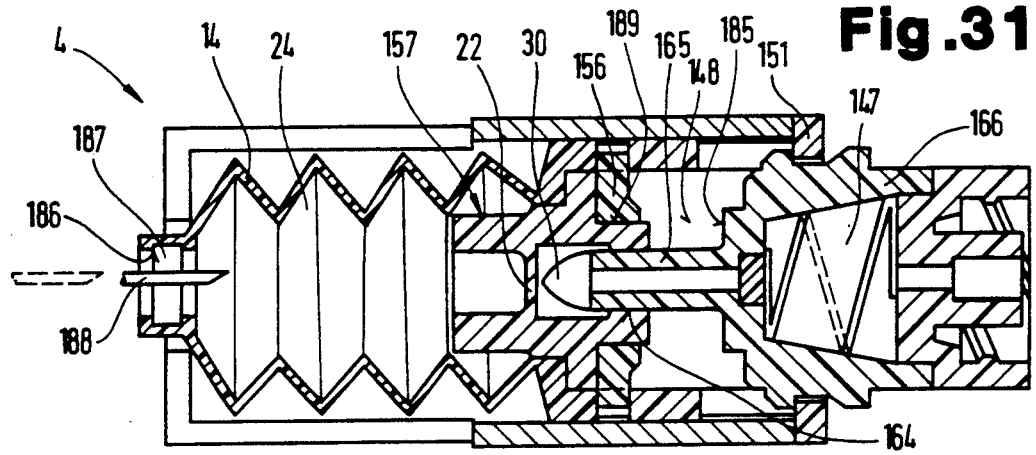
Figure 32:
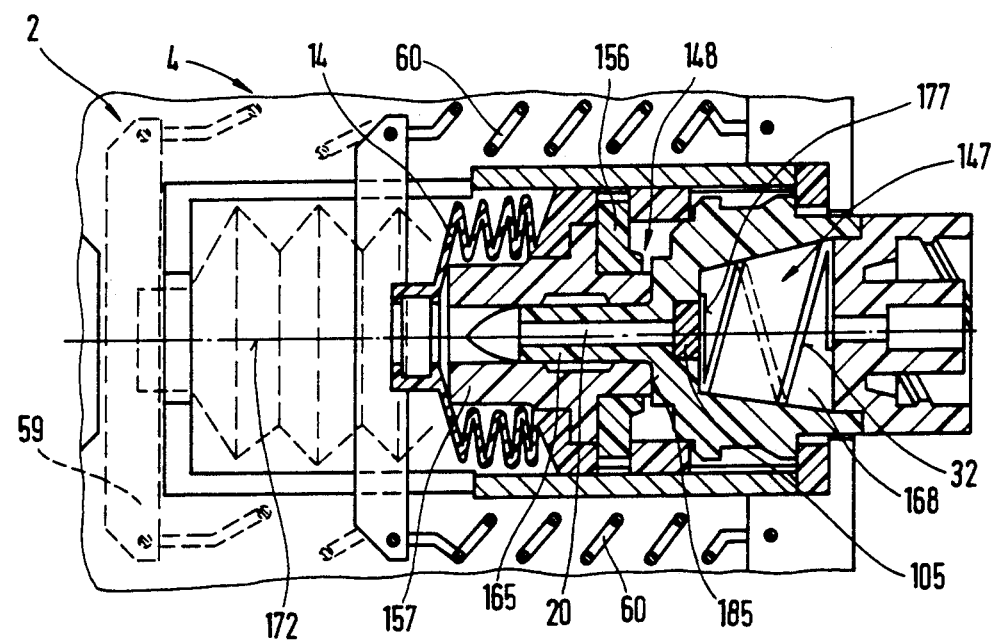
Figure 30:
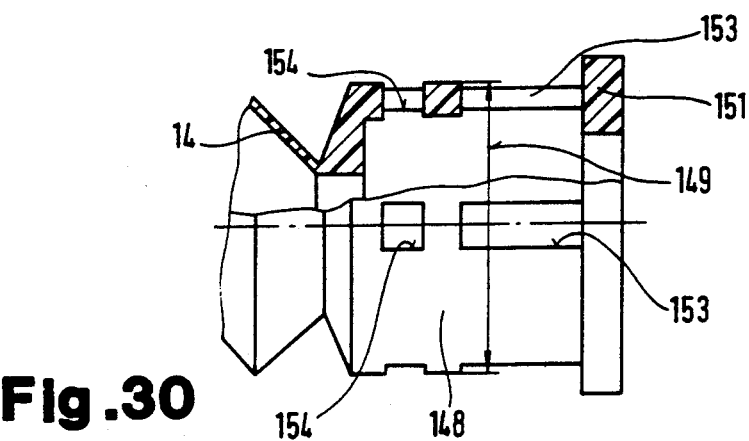

Various embodiments of the invention will now be described in detail with reference to the drawings, wherein FIG. 1 is a partly sectional schematic illustration of an injection device in accordance with the invention, FIG. 2 is a side view of and section along the lines II—II in FIG. 1 through an ampoule in accordance with the invention for use in the device in accordance with the invention, FIG. 3 is an end-on view of the ampoule in FIG. 2, FIG. 4 is a top view of a two-part embodiment of the injection device in accordance with the invention, folded together, FIG. 5 is a side view of and a section along the lines V—V in FIG. 6 through the injection device illustrated in FIG. 4, FIG. 6 is a section along the lines VI—VI in FIG. 5 of the injection device, FIG. 7 is a side view of and section through an ampoule in accordance with the invention, FIG. 8 is side view of and section through a support with a square cross-section accommodated in an injection device in accordance with the invention, FIG. 9 is a schematic flow chart illustrating how the activating mechanism of the injection device in accordance with the invention operates, FIG. 10 is a schematic partly sectional side view of an ampoule in accordance with the invention associated with a needle holder, FIG. 11 is a partly sectional side view of another embodiment of an injection device in accordance with the invention, FIG. 12 is a side view of and section through part of an injection device in accordance with the invention, FIG. 13 is an end-on view of and section along the lines XIII—XIII through the injection device illustrated in FIG. 12, FIG. 14 is a side view of and section through the needle holder in an injection device with an integrated constricting channel and microfilter, FIG. 15 is an end view of and section along the lines XV—XV through the needle holder illustrated in FIG. 14, FIG. 16 is a side view of and section through a microfilter for an injection device, FIG. 17 is an end view of and section along the lines XVII—XVII through the microfilter illustrated in FIG. 16, FIG. 18 is a side view of and section through the parts of the microfilter while the filter membrane is being inserted into it, FIG. 19 is a side view of and section through the parts of the microfilter just after the filter membrane has been inserted into it, FIG. 20 is a schematic partly sectional side view of part of an injection device with a microfilter inserted in it, FIG. 21 is a schematic illustration of an injection device with a different embodiment of a motion-arresting mechanism with the cap open and without an ampoule, FIG. 22 is a schematic illustration of the injection device illustrated in FIG. 21 with the ampoule inserted through the open cap, FIG. 23 is a schematic illustration of the injection device in FIG. 21 with the cap closed, FIG. 24 is an end view of and section through part of the injection device illustrated in FIGS. 21 through 23, FIG. 25 is a schematic illustration of an embodiment of the injection device intended for single use, FIG. 26 illustrates part of the injection device illustrated in FIG. 25 with the ampoule ready to release the medicament, FIG. 27 is a top view of and section through another embodiment of an ampoule being shipped, FIG. 28 illustrates the ampoule illustrated in FIG. 27 activated, FIG. 29 is a top view of the choking mechanism in the ampoule illustrated in FIGS. 27 and 28, FIG. 30 is a sectional top view of part of the main section of the ampoule illustrated in FIGS. 27 and 28, FIG. 31 is a sectional top view of another embodiment of an ampoule, and FIG. 32 is a sectional top view of the ampoule illustrated in FIG. 32 with part of the housing on the injection device, ready to inject medicament.

FIG. 1 illustrates an injection device 1 consisting of a housing 2 with a holder 3 for an ampoule 4. The ampoule has a hypodermic needle 5 at one end and an activating mechanism 6 at the other. Activating mechanism 6 comprises a piston 7 that slides along the longitudinal axis 10 of ampoule 4 inside housing 2 and toward hypodermic needle 5 subject to a piston rod 8 that has a handle 9. The holder 3 in housing 2 has a bore with a thread 11, into which ampoule 4 can be screwed with its outer thread 12. Outer thread 12 is on a tubular support 13. Accommodated in support 13 is a main ampoule section 14 in the form of a bellows. A combination seal and holder 15 that is attached to the main section of the ampoule is also attached to support 13 by a weld 16 for example, an ultrasonic weld for instance. The conbination seal and holder consists of two parts 17 and 18, which may also be attached together by a layer 19 of adhesive or by welding. Parts 17 and 18 have bores 20 and 21 that are coaxial with longitudinal axis 10. Between parts 17 and 18 is a barrier 22 in the form of a diaphragm or membrane for example of pharmaceutical rubber or a similar material in the form of a sealing disk. The barrier prevents the schematically represented medicament 23 from escaping from the space 24 inside ampoule 4. Part 18 is also connected by way of a coupler 25 to a holder 26 that secures hypodermic needle 5. A coupling component 27 in part 18 consists of an inside thread and a coupling component 28 associated therewith consists of an outside thread on needle holder 26. Facing the needle holder from the direction of ampoule 4 is a perforator 29 that has a point 30 for breaking through barrier 22 and an opening 31 that connects the space 24 inside ampoule 4 with hypodermic needle 5. When needle holder 26 is screwed into part 18 of combination seal and holder 15 until it comes to a stop, point 30 will break through the barrier 22 in the form of a sealing disk and will penetrate into the space 24 inside ampoule 4 or the associated bore 20 in part 17 of the combination seal and holder 15, allowing the medicament 23 to enter hypodermic needle 5 through opening 31.

Once the barrier 22, which acts as a safety seal, has been broken through, piston 7 can be forced toward hypodermic needle 5, compressing ampoule 4 or its main section 14, which is a bellows of deformable plastic-pharmaceutical rubber, silicone, or a similar material for example-and injecting medicament 23 out through hypodeermic needle 5.

It is preferable for main ampoule section 14 to be made in one piece with part 17 of a resiliently deformable plastic, silicone for example, whereas part 18, which never comes into contact with the medicament, can be made from a more stable and rigid plastic, PVC or a similar material for example. The greater strength and rigidity of part 18 will render it a better backing for needle holder 26 while barrier 22 is being broken through and while hypodermic needle 5 is being inserted.

To allow the flow of medicament 23 to be controlled while it is being forced out of the space 24 inside ampoule 4 independent of the pressure exerted by activating mechanism 6, needle holder 26 can have a constricting channel 32 that communicates with a bore 33 that communicates with opening 31 in perforator 29 and connects it with the lumen 34 in hypodermic needle 5. Depending on the cross-section of constricting channel 32, which may for example have a diameter of 0.02 mm, the flow of medicament per unit of time can be maintained at a prescribed level.

To facilitate screwing needle holder 26 into part 18, the needle holder can have ribs 35, as can the area around part 18 in support 13.

FIGS. 2 through 6 illustrate another embodiment of an injection device 1 and ampoule 4. This embodiment comprises a tubular or sleeve-like support 13, a combination seal and holder 15, which is in one piece in this case, a barrier 22 consisting of a diaphragm, which can be made from pharmaceutical rubber for example, and a main ampoule section 14 in the form of a bellows. The bellows is made from an elastic plastic approved for keeping medicaments, silicone plastic for example, and the end facing combination seal and holder 15 is surrounded by an annular flange 36. This flange is cemented or welded to one face 37 of combination seal and holder 15 that is made from a rigid plastic, PVC for example. The outside diameter of annular flange 36 can, as illustrated, be slightly longer than one outside diameter of main ampoule section 14, or the inside diameter 39 of support 13 in the vicinity of section 14 can be slightly longer than the outside diameter 38 of section 14. Combination seal and holder 15 can also have an outside diameter 40 that is slightly longer than inside diameter 39. Combination seal and holder 15 can accordingly be precisely positioned in support 13. A needle holder 41 has a hypodermic needle 5 that extends perpendicular to the longitudinal axis 10 of ampoule 4. The needle is protected before being used with a needle protector 42. A perforator 29 of the type described in the present applicants' WO-A1 86/03126 for example can be positioned between needle protector 42 and needle holder 41. Between needle holder 41 and ampoule 4 is a spacer 43. Constricting channel 32 is accommodated in spacer 43 and opens into a channel 44 in needle holder 41 that communicates in turn with the lumen 34 in hypodermic needle 5. The inlet into constricting channel 32 communicates with the bore 33 in perforator 29, which consists of a sharp pin, that opens into the opening 31 in that pin.

The spacer 43 and the needle holder 41 in the present embodiment constitute one component. It is, however, also possible for the two components to be separate and fastened together with a bayonet connection or similar structure. A coupling component 28, which is identical with the coupler 25 illustrated in FIG. 1, is positioned on spacer 43.

As will also be evident from this figure, support 13 has a track 45 in the form of a slots 46.

As will be especially evident from FIG. 3, the slots 46 that constitute track 45 are positioned on a diametrical 47. Track 45 parallels longitudinal axis 10 and, as will now be described with reference to FIGS. 4 through 6, helps to position the mechanism that activates main ampoule section 14.

FIGS. 4 through 6 illustrate an injection device 48 that is intended to accommodate the ampoule 4 illustrated in FIGS. 2 and 3. It comprises a lower housing half 50 and an upper housing half 51 articulated together by way of a hinge 52. Housing halves 50 and 51 are kept closed by a schematically represented snap-together connection 53. Ampoule 4 is positioned in lower housing half 50 between positioning strips 54. Needle holder 41 and spacer 43 are, as will be evident from the figure, coupled to ampoule 4 as the ampoule is inserted. The two parts are for this purpose screwed into coupler 25 until perforator 29 breaks through barrier 22, the diaphragm, that is, and opening 31 is, as will be evident from FIG. 5, in the space 24 inside main ampoule section 14. Since needle protector 42 travels through an opening 56 in a base plate 55 while ampoule 4 is being inserted, hypodermic needle 5 will project beyond the plate. Once ampoule 4 has been correctly positioned, upper housing half 51 is folded up, securing ampoule 4 in place by means of the positioning strips 57 from above as well. As will be more evident from FIGS. 4 and 6, a piston 58 positioned on a transverse strut 59 is associated with the end of tubular support 13 that faces away from the combination seal and holder. Transverse strut 59 is connected to an activating mechanism 61 by way of springs 60 on each side of ampoule 4 that are secured at the end facing away from transverse strut 59 to lower housing half 50. Springs 60 can be helical springs for example. Transverse strut 59 is secured in the position represented by the continuous lines in FIG. 4 by straps 62 that are also part of activating mechanism 61. As will be evident in particular from FIG. 6, the transverse strut has carriers 63 that can shift it toward the position represented by the continuous lines against the force of springs 60. The retaining pins 64 illustrated in FIG. 6 simultaneously deform an arm 65 on strap 62 against the force of a resilient arm 66 and toward ampoule 4. Once retaining pin 64 has arrived in its final position, arm 65 can spring back into the position represented by the continuous lines in FIG. 4, arresting the motion of transverse strut 59 against the force of springs 60 in the position represented by the continuous lines.

Once upper and lower housing parts 50 and 51 have been secured together, activating mechanism 61 can be brought into operation by forcing the buttons 67 that project out on both sides of lower housing half 50 toward ampoule 4, deforming strap 62 around a point 68, and arm 65 releases retaining pin 64, allowing springs 60 to force transverse strut 59 toward opening 56 or combination seal and holder 15. The pressure exerted by piston 58 by way of springs 60 now forces the medicament 23 in ampoule 4 toward hypodermic needle 5. Once needle protector 42 has been removed, the user can insert the needle into the lower arm for example and secure the housing for example to the body, at the arm or leg for instance, with the schematically illustrated strip 69, similar to a watch strap or rubber sleeve. Springs 60 will, in conjunction with constricting channel 32 and in accordance with the amount of medicament in the ampoule, administer the medicament in ampoule 4 to the patient uniformly over a prescribed period of time. This injection device can accordingly be employed to great advantage with patients, diabetics for example, who constantly require low doses over a long period of time to provide the desired therapeutic effect.

Injection device 48 can be secured in place better if lower housing half 50 is provided with skin-compatible adhesive tape 70 to prevent painful displacement of hypodermic needle 5 when the patient moves around.

To provide the patient, the nursing staff, or the physician with an overview of the amount of medicament already administered, the end of carriers 63 that face upper housing half 51 can be colored and viewed through a window 71 provided as illustrated in FIG. 4 with a scale 72 displaying the amount of medicament already administered or still in ampoule 4.

Once ampoule 4 is empty and transverse strut 59 or piston 58 has arrived at the final position represented by the broken lines in FIG. 4, a new ampoule must be introduced. Housing 49 is opened, and transverse strut 59 is forced back along with carriers 63 into the starting position represented by the continuous lines and stopped by strap 62, subsequent to which ampoule 4 is removed and needle holder 41 and spacer 43 screwed out of combination seal and holder 15 if necessary for use in a new ampoule 4.

To prevent the patient, the nursing staff, or the physician from overlooking the time when medicament 23 is completely out or when no more medicament can be extracted from ampoule 4, a limit switch 73 can be associated with the ampoule or with transverse strut 59, in upper housing half 51, and with a source of power, a battery for instance, controls 75, and an adder 76. When limit switch 73, which can be a mechanically activated microswitch, an electromagnetic proximity switch, a light barrier, or a similar device, is triggered by transverse strut 59, controls 75 will activate adder 76, notifying the user audially or, as schematically illustrated, visually with a small flashing light-emitting diode too, of an injection device that the medicament is out. Controls 75 of this type with a limit switch of course are not absolutely necessary, but can be employed in an injection device 48 in conjunction with window 71 or even without a window.

As illustrated by way of example in FIG. 3, needle holder 41 can be separated by a plane paralleling longitudinal axis 10. Constricting channel 32 will in this case be for example a depression in the part of needle holder 41 that is on the right in FIG. 3 and will be covered up by the other half of needle holder 42. The two parts of needle holder 41 are cemented or ultrasonically welded together as part of the manufacturing process. Bore 33 can then be positioned with half in each part of needle holder 41.

FIG. 7 illustrates another version of an ampoule 4. Like the ampoule illustrated in FIG. 2, this ampoule 4 has a support 13 and a main ampoule section 14 consisting of a bellows. Secured in the ampoule's combination seal and holder 15 by way of a coupler 25 is a needle holder 77. Mounted in needle holder 77 and protected by a needle protector 42 is a hypodermic needle 5. A barrier 22 in the form of a diaphragm can be broken through with a perforator 29 in the form of a pressure-application pin 78 with a point 30 at the front. Pressure-application pin 78 can be secured in the position represented by the continuous lines by a tear-off ring 79. To extract medicament 23 from ampoule 4, tear-off ring 79 is ripped off, allowing pressure-application pin 78 to move freely toward main ampoule section 14. Point 30 breaks through barrier 22 and medicament 23 can flow through constricting channel 32, which is in the form of a depression in the surface of pressure-application pin 78, to the lumen 34 in hypodermic needle 5. Constricting channel 32 is designed such that, when pressure-application pin 78 is all the way in, in the position represented by the broken lines, the outlet from constricting channel 32 will communicate directly with the lumen 34 in hypodermic needle 5.

An additional sealing disk 80 can be positioned between the activation end of pressure-application pin 78 and needle holder 77 to prevent medicament from emerging toward the activation end of the piston rather than into lumen 34.

FIG. 8 illustrates an injection device 81 that, like the devices illustrated in FIGS. 2 through 6, has a housing 49 consisting of a lower housing half 50 and an upper housing half 51. A transverse strut 59 is accommodated along with piston 58 in the housing. As will be evident from the figure, the main ampoule section 14 has a round cross-section, whereas the support 82 that accommodates the section has a square cross-section, although it can also have a rectangular or polygonal cross-section. One inner dimension 83 of support 82 equals the diameter of an enveloping circle 84 tangent to the inner surfaces of support 82 and is slightly longer than the outside diameter 38 of main ampoule section 14. The transverse strut 59 in this embodiment is activated by fluid-driven piston-and-cylinder mechanisms 85, with cylinder chambers that face away from ampoule 4 and communicate with a pressure reservoir 86 for the fluid. This particular pressure reservoir 86 for example contains a rubber balloon that exerts a variable pressure on the fluid. As transverse strut 59 returns to the position represented by the continuous lines in FIG. 4, the fluid is forced out of piston-and-cylinder mechanisms 85 and into pressure reservoir 86 and, once transverse strut 59 has been released by the pivoting straps 62, which can be positioned as described in FIGS. 4 through 6, forces piston 58 toward ampoule 4.

It is of course also possible, however, to position an air pump in the housing 49 of injection device 81 and supply it with power from a battery or from an external source. Appropriate control valves can make it possible to force transverse strut 59 in the correct direction for forcing medicament out of ampoule 4 and back into its starting position.

FIG. 9 is a schematic flow chart of a system for operating piston-and-cylinder mechanisms 85. This system has, in addition to pressure reservoir 86, a fluid pump 87, for oil or even air for example. The fluid can be forced through a control valve 88 from pressure reservoir 86 or fluid pump 87 as desired and into the cylindrical chambers of the two piston-and-cylinder mechanisms 85, which are separated by the pistons. The pistons in the two piston-and-cylinder mechanisms 85 are connected by transverse strut 59. At each limiting position of transverse strut 59 is a limit switch 73 that is coupled by way of controls 75 to the mechanism that drives fluid pump 87 and the mechanism 89 that drives control valve 88. Manual activation of control valve 88 or automatic activation of controls 75 by way of buttons 90 will shift piston-and-cylinder mechanisms 85 in the desired way, with the transverse strut 59 moving toward the limit switch 73 nearer controls 75 and forcing the medicament out of ampoule 4, whereas the mechanisms will restore transverse strut 59 to its starting position as they move in the other direction.

It is of course also possible for controls 75 to monitor the level of ampoule 4 as already described in detail with reference to FIG. 4.

FIG. 10 illustrates another embodiment of an ampoule 4. This ampoule comprises a sack-like main section 91 of silicone with an annular flange 36 around the end facing a combination seal and holder 15. Combination seal and holder 15 is constituted by a slide-like component of hard and rigid plastic that the annular flange 36 is fastened to by welding, cement, or clamps. Combination seal and holder 15 accommodates a barrier 22, an elastic diaphragm for example, that can be broken through by the perforator 29 on a needle holder 92. Needle holder 92 has, like those in the previously described embodiments, a hypodermic needle 5, which can be injection-molded into the holder. The needle holder 92 also has the constricting channel 32 described with reference to the previous embodiments.

The sack-like main ampoule section 91 is inserted in a support 93 and connected to main ampoule section 91 in the vicinity of annular flange 36.

The medicament in ampoule 4, which can be transparent to allow the level of medicament therein to be monitored at any time, is forced out by a plunger 94 that folds back main ampoule section 91, forcing medicament 23 out through hypodermic needle 5.

FIG. 11 illustrates an injection device 95 with a housing 96 that accommodates a piston rod 97 and piston 98. The housing has a recess 99 that is wider and longer than the diameter or length of the support 13 for ampoule 4. Once ampoule 4 has been inserted into the recess 99 in housing 96, piston 98 forces it toward hypodermic needle 5 and into housing 96 and encounters the point 30 of perforator 29, which is in the form of a needle and breaks through the safety seal or diaphragm in combination seal and holder 15 so that, as piston 98 continues to advance toward hypodermic needle 5, the medicament can be injected through the needle. Housing 96 can as is suggested be provided with opposing holders to improve the support of housing 96 in the hand.

It is of course also possible to provide controls 75 with sensors 100 like those schematically illustrated in the lower housing half 50 in FIG. 4 or in strip 69 and connected to controls 75 by lines. Sensors 100 can be employed to detect pulse rate, blood pressure, or such other physical data as temperature etc. allowing a computer in controls 75 to monitor the condition of the patient so that the flow of medicament can be increased or decreased in accordance with the data. Any sensors available at the current state of the art for determining temperature, pulse rate, blood pressure, etc. can of course be employed.

It is also within the scope of the invention for sensors 100 to include a motion sensor that detects activity on the part of the patient. This makes it possible to administer more medicament during active periods of the day, especially when the patient is engaging in sports or moving around more, than during periods when he is at rest, sleeping for example. It is of course also possible to exploit movement-powered mechanisms like those employed in watches, to drive the activating mechanism or to utilize the accordingly derived resilient force to operate a pump or such other activating mechanisms as an electric generator or spring. FIG. 12 illustrates an ampoule 4 for an injection device 1 that can be similar to the ampoule illustrated in FIG. 2. The same reference numbers are employed for similar parts. A barrier 22 in the form of a rubber diaphragm is accommodated in a combination seal and holder 15. Combination seal and holder 15 is tightly connected to main ampoule section 14. Barrier 22 is broken through by a perforator 29 in the form of a pointed pin injection-molded into or in one piece with a plastic needle holder 41. A bore 33 communicates with a constricting channel 32 created by ultrasonically welding the two parts 101 and 102 of the needle holder together.

As will be particularly evident from FIG. 13, the constricting channel 32 in part 101 of needle holder 41 is a meandering line of several concentric annular-channel segments extending over an angle of 320° and radially communicating through transverse channels. The annular channel with the longest diameter has an outlet bore 103 with a connection 104 that opens into hypodermic needle 5. The number of annular-channel segments can be varied to control the length of constricting channel 32 and hence the time during which medicament can be forced out of main ampoule section 14 and into hypodermic needle 5. The design of constricting channel 32 will accordingly establish the indication for a medicament administered with an injection device in accordance with the invention.

FIG. 14 illustrates another embodiment of a needle holder 41 that also consists of two parts 101 and 102. Part 101 also contains a constricting channel 32 that can either be helical as illustrated in FIG. 15 or like the channel illustrated in FIG. 13. It is, however, just as possible for the constricting channel 32 in part 101 of needle holder 41 to be a zig-zag. Part 102 is fastened to perforator 29 and part 101 to hypodermic needle 5. Between the outlet from bore 33 and constricting channel 32 is a microfilter 105 that prevents particles suspended in the medicament or particles of rubber created when the point 30 of perforator 29 breaks through the diaphragm in barrier 22 from entering hypodermic needle 5. It is also intended to prevent any crystals that form in the medicament while it is being stored from entering the needle. Microfilter 105 consists of a securing ring 106 that is surrounded by an elevated annular flange 107 on the side facing part 101. A tensioning gasket 108 has been forced into annular flange 107. Between tensioning gasket 108 and securing ring 106 is a filter membrane 109 that rests on webs 110 positioned in tensioning gasket 108. Webs 110 extend over an opening that tapers out conically toward securing ring 106 and opens into an outlet 111 that opens in turn into a constricting channel 32. This system prevents floating particles, crystals of medicament, or other contaminants from entering constricting channel 32 and clogging it up or traveling on to hypodermic needle 5. This will ensure that the rate of administration of the medicament will not unpredictably decrease to the patient's detriment.

FIG. 15 illustrates how constricting channel 32 can also extend in the form of a helix between bore 33 and outlet bore 103.

FIGS. 16 and 17 illustrate microfilter 105 in a larger scale. Microfilter 105 can consist of a securing ring 106 surrounded by an annular flange 107. Inlet channels 113 that can taper conically for example extend toward filter membrane 109 in a partition between an intake 112 and the membrane. Outlet channels 115 that can also taper conically toward filter membrane 109 extend in a partition between filter membrane 109 and an outlet 114. This system results in a uniform distribution of the medicament entering through intake 112 over the whole surface of filter membrane 109, keeping the flow resistance of microfilter 105 relatively low. Another advantage of inlet channels 113 is that they can simultaneously filter out coarser particles upstream of filter membrane 109.

As will be evident from FIG. 14, inlet channels 113 can also be uniformly distributed in concentric circles for example over the partition between intake 112 and filter membrane 109. It is preferable for outlet channels 115 to be displaced to one side of inlet channels 113 as represented by the discontinuous lines in FIG. 17, so that the medicament must permeate filter membrane 109 not only perpendicularly but also radially, which makes such a filter even more effective.

FIGS. 18 and 19 illustrate how a filter membrane 109 of this type, with a diameter of 1 to 2 mm for example, can be inserted between securing ring 106 and tensioning gasket 108. Securing ring 106 and tensioning gasket 108 are positioned on opposite sides of a strip 116 of filter membrane. The strip is secured between the two parts and, as schematically indicated by the arrows in FIG. 18, tensioning gasket 108 is applied to strip 116 from below and securing ring 106 is forced against tensioning gasket 108 from above. An inside edge 117 of annular flange 107 acts like a punch and stamps a filter membrane 109 of the desired diameter out of strip 116, simultaneously forcing it against the tensioning gasket 108 below strip 116. Since securing ring 106 and tensioning gasket 108 are forced together and filter membrane 109 is stamped out of strip 116 almost simultaneously, filter membrane 109 will be precisely cut to size and positioned in microfilter 105. It will accordingly no longer be necessary to provide such tiny filter membranes 109 and insert them between securing ring 106 and tensioning gasket 108 in a separate operation. Microfilter 105 can on the other hand also very simply be injection-molded or expanded into larger plastic components, which provides many new applications for such a microfilter, especially in medical technology.

FIG. 20 illustrates an injection device 118 with an ampoule 119 made of glass for example. Ampoule 119 accommodates a piston 120 at one end. At the other end of ampoule 119 is a Luer cone 121. Accommodated in the Luer cone is a rubber component 122 that simultaneously constitutes a seal between one edge 123 of Luer cone 121 and a component 124 that supports a needle holder. Supporting component 124 is attached by snapin fingers 125 to an annular flange 126 on the face of ampoule 119. A retaining component 127 extends beyond rubber component 122 toward an outlet opening 129 that is blocked off by a protective cap 128. Retaining component 127 is made from a rigid plastic that one end of the needle holder can be inserted into once protective cap 128 has been removed. Injection-molded into retaining component 127 is a microfilter 105, which ensures that, once stopper 128 has been removed and the needle holder inserted, piston 120 will as it moves toward microfilter 105 force the medicament into the hypodermic needle only through microfilter 105. This approach prevents contaminants and crystals or similar structures in the medicament from entering hypodermic needle 5 and hence the patient's body and circulatory system.

The risk of thromboses from foreign particles washed into the circulatory system with intravenously administered medicaments is in particular eliminated.

FIGS. 21 through 24 illustrate another embodiment of an injection device 1. Since this embodiment is simply another version of the embodiments previously described herein, similar parts will be labeled with the same number. Injection device 1 consists of a tub-shaped lower housing half 50 and of an upper housing half 51 that is articulated to one longitudinal edge of the lower half by a hinge 52 and constitutes a lid. Lower housing half 50 accommodates an activating mechanism 6 that consists of a tension spring 60 on each side of ampoule 4. The springs are positioned on each side of an ampoule-accommodating space below slides 131 that extend along the walls of lower housing half 50. Part of each slide 131 can be a resilient pivoting structure 132 that has mounted on it a stop 133 that projects beyond the surface of slides 131. U-shaped guides 134 on the side of ampoule 4 travel back and forth along slides 131 in the directions indicated by double-headed arrow 135. Guides 134 are connected at one end by transverse strut 59, which is secured to the ends of springs 60. The other ends of springs 60 are anchored to a wall 136 of lower housing half 50 that faces transverse strut 59. Stop-engaging surfaces 137 on guides 134 are forced by tensioned springs 60 against stops 133, arresting the motion of guides 134 and transverse strut 59. Positioned on the surface of the upper housing half 51, which functions in the capacity of a lid, that faces in when the housing is closed are punches 138 that operate in conjunction with stopping surfaces 139 on pivoting structures 132. Once an ampoule 4 has been inserted into the space 130 between wall 136 and transverse strut 59, springs 60 will remain tensioned until lid-like upper housing half 51 is closed. When upper housing half 51 is closed, punches 138 force pivoting structures 132 out of the position represented by the continuous lines in FIG. 24 and toward lower housing half 50, lowering the stops 133 on pivoting structures 132 below the surface of slides 131 into the position represented by the broken lines in FIG. 24. The recesses that constitute the stop-engaging surfaces 137 of the U-shaped guides 134 that engage slides 131 are accordingly released, and transverse strut 59, which is rigidly secured to U-shaped guides 134 exerts a force on ampoule 4 or main ampoule section 14 toward wall 136 by way of springs 60.

If ampoule 4 is inserted in the space 130 between wall 136 and transverse strut 59 in such a way that the strut occupies the same area as or engages slot 46, the downward pressure will, immediately after upper housing half 51 has been closed and U-shaped guides 134 are released, compress the bellows structure of ampoule 4 and hence inject the supply of medicament therein.

It is on the other hand also possible to insert ampoule 4 in space 130 in such a way that transverse strut 59 will come to rest against support 13. In this case, no medicament will be forced out of ampoule 4 once upper housing half 51, the lid, has been closed and stops 133 released because no relative motion between transverse strut 59 and support 13 is possible. To force medicament out of ampoule 4 it will be necessary to rotate support 13 until slots 46 completely overlap transverse strut 59. Transverse strut 59 will accordingly be able to exert a force on main ampoule section 14 and compress it, forcing the stored supply of medicament out of main ampoule section 14. Ampoule 4 can be twisted by turning a component of the ampoule that projects out of housing 2, a nipple 140 for example, until transverse strut 59 snaps into slots 46. Ampoule 4 can on the other hand also be twisted by way of a coupling component 141 that is motionally connected to the nipple 140 on ampoule 4 by way of a thread or snap fastener into the position that allows medicament to be forced out of main ampoule section 14. Coupling component 141 communicates with hypodermic needle 5, through which medicament can be injected into the patient, by way of flexible tubing.

This particular embodiment, wherein the medicament is forced out by twisting ampoule 4 is advantageous because for example an ampoule 4 can be inserted into housing 2 at leisure and, in the event of an emergency, injection device 1 can be activated with a rapid twist.

It is of course possible to employ instead of the stop described in FIGS. 21 through 23 stops 133 that have other types of structure or rotate in the other direction. It is for example possible to provide slide 131 with an opening that is just large enough to allow a stop 133 to project from below the slide into the vicinity of U-shaped guides 134. If punches 138 are appropriately positioned outside the path of motion of U-shaped guides 134, the stop will be mounted on lower housing half 50 independent of slides 131 and can be pivoted or adjusted perpendicular to the floor of lower housing half 50. If the punches are appropriately designed it will also be possible to rotate the stop 133 associated with one or both slides 131 out of the path of U-shaped guides 134, around axes perpendicular to the floor of lower housing half 50 for example.

FIGS. 25 and 26 illustrate another embodiment of an injection device 1 in the form of one-way administration apparatus. An ampoule 4 is accommodated between wall 136 and transverse strut 59 inside a housing that can for example be made of two parts sealed or welded together. Transverse strut 59 is positioned and operated essentially as described with reference to FIGS. 21 through 24 and differs therefrom only by the absence of stops 133 and pivoting structures 132. Ampoule 4 is secured in its position in housing 2 by the tension exerted on transverse strut 59 by springs 60, which forces the ampoule by way of support 13 against opposite wall 136. Ampoule 4 is inserted in such a way that slots 46 and transverse strut 59 rotate toward each other and the springs 60 in activating mechanism 6 are tensioned. A nipple 140 that blocks the coupling component 141 in a cannula 143 projects out of a hole 142 in wall 136. Either nipple 140 or coupling component 141, which is screwed into it or snapped or bayonetted to it in such a way that it will move along with it, can be adjusted in the direction indicated by arrow 144 in relation to main ampoule section 14 or support 13 along the axis of ampoule 4. During this adjustment or during the welding [sic!—translator] of nipple 140 in the direction indicated by arrow 144, the barrier 22 in the combination seal and holder 15 for ampoule 4 is pierced and broken through. If coupling component 141, once it has been advanced along the axis of ampoule 4 even though it is also secured non-rotating to support 13, is rotated around the longitudinal axis of the ampoule, transverse strut 59 will, once support 13 has been rotated far enough in relation to transverse strut 59, engage slots 46. This will occur once the supporting structure or nipple 140 has been rotated out of an initial position 145 and into another position 146 in relation to housing 2. Once support 13 is in second position 146, transverse strut 59 will engage slots 46 and will be advanced by the force of the spring toward wall 136. This will compress main ampoule section 14 and inject the medicament through cannula 143.

FIGS. 27 through 30 illustrate another version of an ampoule 4 with a choking mechanism 167. The same numbers are employed for similar parts.

The main section 14 of an ampoule 4 is in the shape of a bellows and is accommodated in a support 13. Main ampoule section 14 is secured in support 13 by a cylindrical projection 148 with an outside diameter 149 (FIG. 30). Outside diameter 149 is essentially equal to or longer than the inside diameter 150 of support 13, ensuring that main ampoule section 14 will fit tight in support 13. The cylindrical projection has, as will be particularly evident from FIG. 30, an annular stop 151 that comes to rest against one face 152 of support 13 to position main ampoule section 14. As will be particularly evident from FIG. 30, cylindrical projection 148 has slots 153 distributed along its circumference and perforations 154 that are longitudinally separated from them and also distributed along the circumference. The purpose of perforations 154 is, in conjunction with matching projections 155, to accommodate a pressure-application plate 156. This plate forces a stopper 157 that constitutes combination seal and holder 15 into a retaining flange 158 on main ampoule section 13 and secure it tight against that flange. The distance 159 (FIG. 27) between the retaining flange 158 on main ampoule section 13 and the facing surface 160 of pressure-application plate 156 is shorter than the thickness of a supporting ring 161 on stopper 157 when not subject to tension. The result is secure and tight contact and a satisfactory fit between stopper 157 and the retaining flange 158 in main ampoule section 13. Stopper 157 also has a continuation 162 that extends into the space 24 inside main ampoule section 13 and is provided with a bore 163 that is sealed off from pressure-application plate 156 by barrier 22, which can for example be a thin film of the same plastic that stopper 157 is made of. Accommodated in an alignment bore 164 that is concentric with bore 163 is a cylindrical extension 165 with a point 30 that faces barrier 22. Cylindrical extension 165 is preferably in one piece with a structure 166. Structure 166 accommodates a choking mechanism 167 in the form of a truncoconical choking structure 168 that fits in a truncoconical recess 169. Choking structure 168 is secured in position by a nipple 170 that fits into accommodating structure 166 and is secured to accommodating structure 166 by an ultrasonic weld 171 in such a way that it moves along with it. The passage of the medicament 23 in the space 24 inside ampoule 4 can be impeded by a constricting channel 32 at the circumference of choking structure 168.

As will be particularly evident from FIG. 29, constricting channel 32 is concentric with the longitudinal axis 172 of main ampoule section 14 and consists of depressions that extend around the surface of choking structure 168 with their beginning 173 and end 174 separated along the circumference by an angle of between 10° and 45°, preferably 20°. The end 174 of one constricting-channel section 176 communicates with the end 174 of another constricting-channel section 176 that is farther away toward longitudinal axis 172 by way of a communicating channel 177 in the form of depression that extends toward a generatrix in the truncoconical surface. The end 174 of the second constricting-channel section 176 is similarly connected to the beginning of another constricting-channel section 178. As will also be evident from FIGS. 27 through 29, a supply line in the form of bore 20 communicates by way of a radial communicating channel 179 with the nearest constricting-channel section 176. One constricting-channel section 180 communicates by away of an also radial communicating channel 177 with an outlet channel 181 through the center of nipple 170.

The design of constricting channel 32 in the form of depressions in the surface of retaining flange 158 results, due to the conical surface in conjunction with the conical shape of recess 16, to an unobjectionable seal between the separate constricting-channel sections 176, 178, and 180 and their associated communicating channels 177 and 179. This seal is also sufficient to ensure a seal between the constricting-channel sections at a high pressure in the medicament.

The same result can of course be attained by positioning the depressions for constricting-channel sections 176, 178, and 180 and communicating channels 177 and 179 in the recess 169 in accommodating structure 166.

Another advantage of this embodiment of the invention is that main ampoule section 14 can be inserted into support 13 until it comes into contact with the annular stop 151 on the face 152 of support 13, subsequent to which a medicament 23 can be introduced into the space 24 inside ampoule 4. Once enough medicament has been introduced, stopper 157 is inserted and forced against the retaining flange 158 on main ampoule section 14 by pressure-application plate 156 in such a way as to produce a tight and sterile seal in relation to the space 24 inside ampoule 4. Accommodating structure 166 is subsequently advanced, accompanied by elastic deformation of annular stop 151, by accommodating noses 182 positioned on accommodating structure 166 and associated with slots 153 until annular stop 151 snaps into a depression 183 on accommodating structure 166, as represented by the continuous lines in FIG. 27. Ampoule 4 is accordingly prepared for insertion at any time into the holder 3 in the housing 2 of injection device 1. When the medicament is to be removed from the space 24 inside ampoule 4 it is necessary only to shift accommodating structure 166 as illustrated in FIG. 28 into the position represented by the continuous lines, paralleling longitudinal axis 172 and far enough toward stopper 157 for retainers 184 to come to rest, once annular stop 151 has been resiliently deformed from the direction of main ampoule section 14, against annular stop 151. During this insertion procedure accommodating structure 166 is positioned by accommodating noses 182, preventing obstruction or undesired lateral displacements of cylindrical extension 165. Extension 165 is simultaneously positioned in pressure-application plate 156 by alignment bore 164. The diameter of extension 165 is equal to or slightly less than that of the bore 163 in stopper 157 so that, once barrier 22 has been broken through, there will be a tight seal between extension 165 and stopper 157. The positions of accommodating noses 182, depression 183, and retainers 184 will also ensure that a surface 185 on accommodating structure 166 will come to rest tight against the areas of pressure-application plate 156 that surround alignment bore 164. This is a very reliable method of preventing medicament from leaking out of the space 24 inside ampoule 4 while it is being injected.

FIGS. 31 and 32 illustrate another version of an ampoule 4 that is essentially similar to the embodiment described with reference to FIGS. 27 through 30.

Main ampoule section 14 has a projection 148. To ensure that the prescribed dose can be introduced at any time into the space 24 inside ampoule 4, the side of the main ampoule section 14 that faces away from projection 148 is provided with an opening 186 that is closed off with a disk 187 of permanently resilient silicon, A needle 188 or hypodermic syringe can be inserted through disk 187 to introduce any desired medicament into the space 24 inside ampoule 4. One of the properties of the permanently resilient silicone that disk 187 is made from is that, if needle 188 is extracted into the position represented by the broken lines, the perforation will seal up again and, when the medicament is being forced out of the space 24 inside ampoule 4, it will only be able to flow through choking mechanism 47 once barrier 22 has been broken through by the point 30 of extension 165. This embodiment also ensures that every area of the extension 165 that breaks through barrier 22 and penetrates into space 24 will be kept sterile. Stopper 157 is for that purpose lengthened toward the annular stop 151 of main ampoule section 14 and extends through a bore 189 in pressure-application plate 156. The stopper has in this vicinity the alignment bore 164 for extension 165. Since stopper 157 is made from a sealing material, silicone rubber or a similar compound for example, the joint between extension 165 and alignment bore 164 will be tight, and no germs will be able to penetrate into the vicinity of the point 30 of extension 165. The embodiment also ensures that, once extension 165 has broken through barrier 22, the surface 185 or accommodating structure 166 will rest tight against stopper 157, preventing the escape of medicament while it is being forced out of space 24. The embodiment illustrated in FIGS. 31 and 32 also differs from that described with reference to FIGS. 27 through 29 in that choking mechanism 147 has, instead of the constricting-channel sections concentric with the longitudinal axis 172, a helical constricting channel 32 that extends from one face of choking structure 168 to the opposite face. The medicament is supplied to and removed from the choking mechanism 147 as described with reference to FIGS. 28 and 29.

FIG. 32 illustrates main ampoule section 14 in various positions. The broken lines represent the position of transverse strut 59 and main ampoule section 14 once the section has been inserted in housing 2 but before the medicament starts to be forced out. If the motion of transverse strut 59 is released as described with reference to the foregoing embodiments, transverse strut 59 will be drawn by springs 60 toward choking mechanism 147 and will accordingly compress main ampoule section 14 until it arrives in the final position represented by the continuous lines, in which the desired volume of medicament has been injected out of main ampoule section 14 by way of choking mechanism 147. Main ampoule section 14 is then compressed like an accordion until its individual bulges rest against one another. The amount of medicament remaining in the spaces between the bulges will have been compensated for by increasing the dose, so that the desired amount of medicament will always be available for delivery through choking mechanism 147.

It is naturally within the scope of the present invention to apply the pressure that is to be exerted on main ampoule section 14 by means of compression springs, resting for example against the surface of the housing that faces transverse strut 59 and coupled to the strut by arms. It is also possible to provide such power-driven activators as a hydraulic cylinder or a miniature electric motor and pinion to engage racks or similar structures connected to transverse strut 59. It would also be conceivable to use a system comprising a spindle and traveling nuts as a power-driven activator, in which case it would be preferable for the nuts to be connected to transverse strut 59 in such a way as to displace it.

As also illustrated in conjunction with this embodiment, a microfilter 105 is positioned between communicating channel 177 and bore 20. Its structure and function have already been described.

It is naturally also possible within the scope of the present invention to employ any conceivable type of activating mechanism to empty ampoule 4. It can be positioned inside or outside and connected with lines.

The ampoule or its main section can be made out of any desired material. Care should, be taken to ensure, that only medicament-compatible plastics, silicone for example, are used.

It is naturally also possible within the scope of the invention to employ a microfilter 105 with any of the embodiments described herein. Inventive level is also to be ascribed to the structure of the microfilter and the method of manufacturing it independent of the characteristics of the syringe itself. This also applies to the manufacture of the constricting channel, which can also be employed with syringes that differ from the embodiments described herein and which can be considered an independent inventive solution.

I claim:

1. An injection device for selectively dispensing a small, controlled amount of a medicament into a body of a patient, comprising
   (a) a deformable bag-shaped ampoule having a closed end and an opposite open dispensing end, the ampoule having a longitudinal axis and defining an interior chamber containing the medicament,
   (b) a coaxial support receiving the ampoule between the ends thereof,
   (c) a housing providing an abutment for the ampoule support,
   (d) a hypodermic needle,
   (e) a device for sealing the open ampoule end and for holding the hypodermic needle, the device comprising
      (1) a holding element fixedly held in the support,
      (1) a carrier for the hypodermic needle, the carrier being mounted on the holding element for axial adjustment relative thereto, and
      (2) a piercing device penetrating through the holding element into the interior ampoule chamber upon axial adjustment of the hypodermic needle carrier, the piercing device having an axial bore receiving medicament from the interior ampoule chamber upon penetration thereof by the piercing device, (f) an actuating mechanism for compressing the deformable ampoule and extending into the housing, the actuating mechanism comprising
  (1) a piston slidable in an axial direction towards the sealing and holding device, the piston acting upon the closed ampoule end for compressing the deformable ampoule,
  (2) the support having a guide track extending between the ampoule ends and being arranged for guiding the slidable piston, and (g) a constricted, pressure-regulating channel extending through the hypodermic needle carrier, the channel connecting the interior ampoule chamber to the hypodermic needle through the bore of the piercing device.

2. The injection device of claim 1, wherein the sealing and holding device comprises a spacing element between the holding element and the hypodermic needle carrier, the constricted, pressure-regulating channel extending through the spacing element.

3. The injection device of claim 2, wherein the holding element is affixed to the open ampoule end.

4. The injection device of claim 3, wherein the holding element is comprised of a rigid synthetic resin body and is bonded to the open ampoule end.

5. The injection device of claim 2, wherein the hypodermic needle carrier and spacing element define adjoining faces extending perpendicularly to a longitudinal axis of the ampoule, the constricted pressure-regulating channel being defined by a recess in one of the adjoining faces and facing the other face, the recess being closed by the other face.

6. The injection device of claim 5, wherein the constricted, pressure-regulating channel comprises a plurality of annular channel portions extending concentrically about the longitudinal ampoule axis, the channel portions having different diameters, each channel portion extending over an arc of about 270° and radially alternating ones of the concentric channel portions being connected to each other.

7. The injection device of claim 5, wherein the constricted, pressure-regulating channel extends spirally about the longitudinal ampoule axis.

8. The injection device of claim 1, wherein the holding element is comprised of two parts, further comprising a barrier membrane interposed between the two holding element parts.

9. The injection device of claim 1, further comprising a device for coupling the hypodermic needle carrier to the holding element.

10. The injection device of claim 9, wherein the holding element comprises a threaded socket and the hypodermic needle carrier has a threaded coupling member threadedly attachable to the socket to form the coupling device.

11. The injection device of claim 10, wherein the threaded socket and the threaded coupling member extend parallel to a longitudinal axis of the ampoule extending between the ampoule ends.

12. The injection device of claim 1, further comprising a microfilter arranged between the piercing member and the hypodermic needle, the microfilter having a face facing towards the hypodermic needle and covering the constricted, pressure-regulating channel.

13. The injection device of claim 12, wherein the microfilter comprises a holding ring, a clamping disc and a filter membrane arranged between the holding ring and the clamping disc, the holding ring comprising an annular flange having an inner diameter corresponding an outer diameter of the clamping disc.

14. The injection device of claim 13, wherein the holding ring and the clamping disc have peripheral faces engaged in a friction fit.

15. The injection device of claim 1, wherein the support and the ampoule are tubular, the support having an elongated interior chamber receiving the ampoule.

16. The injection device of claim 1, wherein the guide track extends in the support parallel to the longitudinal axis of the ampoule and the piston has guide elements slidable along the guide track.

17. The injection device of claim 16, wherein the guide track comprises two diametrically opposed elongated grooves in the support.

18. The injection device of claim 1, wherein the actuating mechanism comprises spring drives at respective sides of the support, further comprising a device for arresting the slidable piston in an end position spaced from the support.

19. The injection device of claim 18, wherein the actuating mechanism comprises a transverse strut engaged by the spring drives and the arresting device comprises a catch for holding the transverse strut in position.

20. The injection device of claim 19, wherein the catch is pivotal about an axis extending parallel to the transverse strut.

21. The injection device of claim 20, further comprising a pivotal element carrying the catch, a two-part casing for the injection device, one casing part being a hinged cover, and a pressure button on the cover and aligned with the pivotal element upon closing the cover for pressing upon the pivotal element.

22. The injection device of claim 21, wherein the casing defines an opening wherethrough the hypodermic needle projects.

23. The injection device of claim 1, further comprising a control for the actuating mechanism, the control comprising a sensor for monitoring vital data of the patient.

24. The injection device of claim 23, wherein the control further comprises a motion sensor and a control member responsive to motions monitored by the motion sensor whereby the actuating mechanism compresses the ampoule in response to the monitored motions to deliver a desired amount of the medicament from the ampoule to the hypodermic needle.

25. The injection device of claim 1, further comprising a pressure throttling frusto-conical body having a periphery wherein two circumferential recesses are formed to define portions of the constricted, pressure-regulating channel, the frusto-conical body having a center axis and the recesses extending perpendicularly to the center axis and being spaced from each other therealong, each circumferential recess having a starting and a terminal end spaced from each other by an angle between 10° and 45° in the circumferential direction, and a connecting channel between the starting end of one recess and the terminal end of the other recess.

26. The injection device of claim 25, wherein the connecting channel is a recess in the periphery of the frusto-conical body, the recess extending in the direction of a rectilinear generatrix of the periphery.

27. The injection device of claim 1, further comprising a pressure throttling frusto-conical body having a periphery wherein a spiral recess defines the constricted, pressure-regulating channel.

28. The injection device of claim 1, wherein the holding element comprises a receiving body having a substantially cylindrical periphery and defining a frusto-conical recess, further comprising a pressure-throttling frusto-conical body fitted in the frusto-conical recess and having a periphery defining the constricted, pressure-regulating channel.

29. The injection device of claim 28, further comprising diametrically opposed abutments arranged on the periphery of the receiving body, a pointed elongated cylindrical element projecting from the receiving body away from the frusto-conical recess and towards the sealing member, the cylindrical element defining a central elongated bore, and a cylindrical closure nipple mounted on the receiving body over the frusto-conical recess and body, the nipple being bonded to the receiving body.

* * * * *

UNITED STATES PATENT AND TRADEMARK OFFICE
CERTIFICATE OF CORRECTION

PATENT NO. : 5,147,311
DATED     : September 15, 1992
INVENTOR(S) : Ewald Pickhard (PCT Case 4)

It is certified that error appears in the above-identified patent and that said Letters Patent is hereby corrected as shown below:

Cover page, item 86, lines 2 and 3, correct the Section 371 and Section 102(e) dates to read --May 3, 1990--.

Signed and Sealed this

Twenty-sixth Day of October, 1993

Attest:

BRUCE LEHMAN

Attesting Officer

Commissioner of Patents and Trademarks